US012636435B2

(12) United States Patent (10) Patent No.: US 12,636,435 B2
Williams et al. (45) Date of Patent: May 26, 2026

(54) TECHNIQUES FOR OPTIMIZING USAGE OF AN AUTOMATIC DRUG DELIVERY SYSTEM

(71) Applicant: Insulet Corporation, Acton, MA (US)

(72) Inventors: Joshua Williams, Marlborough, MA (US); Pauline Tandon, Hopkinton, MA (US); Mark Field, Acton, MA (US); Jay Jantz, Acton, MA (US); Steve Lowen, Bedford, MA (US); Rangarajan Narayanaswami, Weston, MA (US)

(73) Assignee: INSULET CORPORATION, Acton, MA (US)

( * ) Notice: Subject to any disclaimer, the term of this patent is extended or adjusted under 35 U.S.C. 154(b) by 1143 days.

(21) Appl. No.: 17/668,509

(22) Filed: Feb. 10, 2022

(65) Prior Publication Data

US 2022/0273873 A1 Sep. 1, 2022

Related U.S. Application Data

(60) Provisional application No. 63/154,164, filed on Feb. 26, 2021.

(51) Int. Cl.
*A61M 5/172* (2006.01)
*G16H 20/17* (2018.01)
(Continued)

(52) U.S. Cl.
CPC .......... *A61M 5/1723* (2013.01); *G16H 20/17* (2018.01); *G16H 50/20* (2018.01); *G16H 50/30* (2018.01);
(Continued)

(58) Field of Classification Search
CPC ...... A61M 5/1723; A61M 2005/14208; A61M 2005/1726; A61M 2205/3303;
(Continued)

(56) References Cited

U.S. PATENT DOCUMENTS 303,013 A 8/1884 Horton
2,797,149 A 6/1957 Skeggs
(Continued)

FOREIGN PATENT DOCUMENTS

AU 2015200834 A1 3/2015
AU 2015301146 A1 3/2017
(Continued)

OTHER PUBLICATIONS

US 5,954,699 A, 09/1999, Jost et al. (withdrawn)
(Continued)

*Primary Examiner* — Laura A Bouchelle
*Assistant Examiner* — Marissa Taylor
(74) *Attorney, Agent, or Firm* — Goodwin Procter LLP

(57) ABSTRACT

The provided examples of systems, devices and techniques improve systems and methods for keeping users of automatic drug delivery systems engaged and assisting with the optimal use of the drug delivery system. The automatic drug delivery system may include a drug delivery device and a controller. Through the use of an attrition prevention engine in a cloud-based services system that cooperates with an attrition prevention application executing on the controller of the drug delivery device, notifications that include instructions for adjusting operation of the drug delivery device as well as offer assistance to the patient to optimize performance of the drug delivery system for the patient may be provided. Optimizing the performance of the drug delivery system has been shown to prevent attrition of patients from using the drug delivery system.

13 Claims, 11 Drawing Sheets

(51) Int. Cl.
    *G16H 50/20*      (2018.01)
    *G16H 50/30*      (2018.01)
    *A61M 5/142*     (2006.01)

(52) U.S. Cl.
    CPC ............. *A61M 2005/14208* (2013.01); *A61M*
        *2005/1726* (2013.01); *A61M 2205/3303*
       (2013.01); *A61M 2205/3569* (2013.01); *A61M*
          *2205/502* (2013.01); *A61M 2230/201*
                      (2013.01)

(58) Field of Classification Search
    CPC .... A61M 2205/3569; A61M 2205/502; A61M
          2230/201; G16H 20/17; G16H 50/30;
                        G16H 50/20
    See application file for complete search history.

(56)             References Cited

U.S. PATENT DOCUMENTS

| | | | |
|---|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute, deceased et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |

(56)  References Cited

U.S. PATENT DOCUMENTS

| | | | |
|---|---|---|---|
| 6,143,164 | A | 11/2000 | Heller et al. |
| 6,157,041 | A | 12/2000 | Thomas et al. |
| 6,161,028 | A | 12/2000 | Braig et al. |
| 6,162,639 | A | 12/2000 | Douglas |
| 6,196,046 | B1 | 3/2001 | Braig et al. |
| 6,200,287 | B1 | 3/2001 | Keller et al. |
| 6,200,338 | B1 | 3/2001 | Solomon et al. |
| 6,214,629 | B1 | 4/2001 | Freitag et al. |
| 6,226,082 | B1 | 5/2001 | Roe |
| 6,244,776 | B1 | 6/2001 | Wiley |
| 6,261,065 | B1 | 7/2001 | Nayak et al. |
| 6,262,798 | B1 | 7/2001 | Shepherd et al. |
| 6,270,455 | B1 | 8/2001 | Brown |
| 6,271,045 | B1 | 8/2001 | Douglas et al. |
| 6,280,381 | B1 | 8/2001 | Malin et al. |
| 6,285,448 | B1 | 9/2001 | Kunstner |
| 6,309,370 | B1 | 10/2001 | Haim et al. |
| 6,312,888 | B1 | 11/2001 | Wong et al. |
| 6,334,851 | B1 | 1/2002 | Hayes et al. |
| 6,375,627 | B1 | 4/2002 | Mauze et al. |
| 6,379,301 | B1 | 4/2002 | Worthington et al. |
| 6,402,689 | B1 | 6/2002 | Scarantino et al. |
| 6,470,279 | B1 | 10/2002 | Samsoondar |
| 6,475,196 | B1 | 11/2002 | Vachon |
| 6,477,901 | B1 | 11/2002 | Tadigadapa et al. |
| 6,484,044 | B1 | 11/2002 | Lilienfeld-Toal |
| 6,491,656 | B1 | 12/2002 | Morris |
| 6,512,937 | B2 | 1/2003 | Blank et al. |
| 6,525,509 | B1 | 2/2003 | Petersson et al. |
| 6,528,809 | B1 | 3/2003 | Thomas et al. |
| 6,540,672 | B1 | 4/2003 | Simonsen et al. |
| 6,544,212 | B2 | 4/2003 | Galley et al. |
| 6,546,268 | B1 | 4/2003 | Ishikawa et al. |
| 6,546,269 | B1 | 4/2003 | Kurnik |
| 6,553,841 | B1 | 4/2003 | Blouch |
| 6,554,798 | B1 | 4/2003 | Mann et al. |
| 6,556,850 | B1 | 4/2003 | Braig et al. |
| 6,558,351 | B1 | 5/2003 | Steil et al. |
| 6,560,471 | B1 | 5/2003 | Heller et al. |
| 6,561,978 | B1 | 5/2003 | Conn et al. |
| 6,562,001 | B2 | 5/2003 | Lebel et al. |
| 6,562,014 | B2 | 5/2003 | Lin et al. |
| 6,569,125 | B2 | 5/2003 | Jepson et al. |
| 6,572,542 | B1 | 6/2003 | Houben et al. |
| 6,572,545 | B2 | 6/2003 | Knobbe et al. |
| 6,574,490 | B2 | 6/2003 | Abbink et al. |
| 6,575,905 | B2 | 6/2003 | Knobbe et al. |
| 6,580,934 | B1 | 6/2003 | Braig et al. |
| 6,618,603 | B2 | 9/2003 | Varalli et al. |
| 6,633,772 | B2 | 10/2003 | Ford et al. |
| 6,645,142 | B2 | 11/2003 | Braig et al. |
| 6,653,091 | B1 | 11/2003 | Dunn et al. |
| 6,662,030 | B2 | 12/2003 | Khalil et al. |
| 6,669,663 | B1 | 12/2003 | Thompson |
| 6,678,542 | B2 | 1/2004 | Braig et al. |
| 6,699,221 | B2 | 3/2004 | Vaillancourt |
| 6,718,189 | B2 | 4/2004 | Rohrscheib et al. |
| 6,721,582 | B2 | 4/2004 | Trepagnier et al. |
| 6,728,560 | B2 | 4/2004 | Kollias et al. |
| 6,740,059 | B2 | 5/2004 | Flaherty |
| 6,740,072 | B2 | 5/2004 | Starkweather et al. |
| 6,751,490 | B2 | 6/2004 | Esenaliev et al. |
| 6,758,835 | B2 | 7/2004 | Close et al. |
| 6,780,156 | B2 | 8/2004 | Haueter et al. |
| 6,810,290 | B2 | 10/2004 | Lebel et al. |
| 6,837,858 | B2 | 1/2005 | Cunningham et al. |
| 6,837,988 | B2 | 1/2005 | Leong et al. |
| 6,846,288 | B2 | 1/2005 | Nagar et al. |
| 6,862,534 | B2 | 3/2005 | Sterling et al. |
| 6,865,408 | B1 | 3/2005 | Abbink et al. |
| 6,890,291 | B2 | 5/2005 | Robinson et al. |
| 6,936,029 | B2 | 8/2005 | Mann et al. |
| 6,949,081 | B1 | 9/2005 | Chance |
| 6,958,809 | B2 | 10/2005 | Sterling et al. |
| 6,989,891 | B2 | 1/2006 | Braig et al. |
| 6,990,366 | B2 | 1/2006 | Say et al. |
| 7,008,404 | B2 | 3/2006 | Nakajima |
| 7,009,180 | B2 | 3/2006 | Sterling et al. |
| 7,016,713 | B2 | 3/2006 | Gardner et al. |
| 7,018,360 | B2 | 3/2006 | Flaherty et al. |
| 7,025,743 | B2 | 4/2006 | Mann et al. |
| 7,025,744 | B2 | 4/2006 | Utterberg et al. |
| 7,027,848 | B2 | 4/2006 | Robinson et al. |
| 7,043,288 | B2 | 5/2006 | Davis, III et al. |
| 7,060,059 | B2 | 6/2006 | Keith et al. |
| 7,061,593 | B2 | 6/2006 | Braig et al. |
| 7,096,124 | B2 | 8/2006 | Sterling et al. |
| 7,115,205 | B2 | 10/2006 | Robinson et al. |
| 7,128,727 | B2 | 10/2006 | Flaherty et al. |
| 7,139,593 | B2 | 11/2006 | Kavak et al. |
| 7,139,598 | B2 | 11/2006 | Hull et al. |
| 7,144,384 | B2 | 12/2006 | Gorman et al. |
| 7,171,252 | B1 | 1/2007 | Scarantino et al. |
| 7,190,988 | B2 | 3/2007 | Say et al. |
| 7,204,823 | B2 | 4/2007 | Estes et al. |
| 7,248,912 | B2 | 7/2007 | Gough et al. |
| 7,267,665 | B2 | 9/2007 | Steil et al. |
| 7,271,912 | B2 | 9/2007 | Sterling et al. |
| 7,278,983 | B2 | 10/2007 | Ireland et al. |
| 7,291,107 | B2 | 11/2007 | Hellwig et al. |
| 7,291,497 | B2 | 11/2007 | Holmes et al. |
| 7,303,549 | B2 | 12/2007 | Flaherty et al. |
| 7,303,622 | B2 | 12/2007 | Loch et al. |
| 7,303,922 | B2 | 12/2007 | Jeng et al. |
| 7,354,420 | B2 | 4/2008 | Steil et al. |
| 7,388,202 | B2 | 6/2008 | Sterling et al. |
| 7,402,153 | B2 | 7/2008 | Steil et al. |
| 7,404,796 | B2 | 7/2008 | Ginsberg |
| 7,429,255 | B2 | 9/2008 | Thompson |
| 7,460,130 | B2 | 12/2008 | Salganicoff |
| 7,481,787 | B2 | 1/2009 | Gable et al. |
| 7,491,187 | B2 | 2/2009 | Van Den Berghe et al. |
| 7,500,949 | B2 | 3/2009 | Gottlieb et al. |
| 7,509,156 | B2 | 3/2009 | Flanders |
| 7,547,281 | B2 | 6/2009 | Hayes et al. |
| 7,569,030 | B2 | 8/2009 | Lebel et al. |
| 7,608,042 | B2 | 10/2009 | Goldberger et al. |
| 7,651,845 | B2 | 1/2010 | Doyle, III et al. |
| 7,680,529 | B2 | 3/2010 | Kroll |
| 7,734,323 | B2 | 6/2010 | Blomquist et al. |
| 7,766,829 | B2 | 8/2010 | Sloan et al. |
| 7,785,258 | B2 | 8/2010 | Braig et al. |
| 7,806,854 | B2 | 10/2010 | Damiano et al. |
| 7,806,886 | B2 | 10/2010 | Kanderian, Jr. et al. |
| 7,918,825 | B2 | 4/2011 | OConnor et al. |
| 7,946,985 | B2 | 5/2011 | Mastrototaro et al. |
| 7,972,296 | B2 | 7/2011 | Braig et al. |
| 8,221,345 | B2 | 7/2012 | Blomquist |
| 8,251,907 | B2 | 8/2012 | Sterling et al. |
| 8,449,524 | B2 | 5/2013 | Braig et al. |
| 8,452,359 | B2 | 5/2013 | Rebec et al. |
| 8,454,576 | B2 | 6/2013 | Mastrototaro et al. |
| 8,467,980 | B2 | 6/2013 | Campbell et al. |
| 8,478,557 | B2 | 7/2013 | Hayter et al. |
| 8,547,239 | B2 | 10/2013 | Peatfield et al. |
| 8,597,274 | B2 | 12/2013 | Sloan et al. |
| 8,622,988 | B2 | 1/2014 | Hayter |
| 8,810,394 | B2 | 8/2014 | Kalpin |
| 9,061,097 | B2 | 6/2015 | Holt et al. |
| 9,171,343 | B1 | 10/2015 | Fischell et al. |
| 9,233,204 | B2 | 1/2016 | Booth et al. |
| 9,486,571 | B2 | 11/2016 | Rosinko |
| 9,579,456 | B2 | 2/2017 | Budiman et al. |
| 9,743,224 | B2 | 8/2017 | San Vicente et al. |
| 9,907,515 | B2 | 3/2018 | Doyle, III et al. |
| 9,980,140 | B1 * | 5/2018 | Spencer ............... H04W 12/02 |
| 9,984,773 | B2 | 5/2018 | Gondhalekar et al. |
| 10,248,839 | B2 | 4/2019 | Levy et al. |
| 10,335,464 | B1 | 7/2019 | Michelich et al. |
| 10,583,250 | B2 | 3/2020 | Mazlish et al. |
| 10,737,024 | B2 | 8/2020 | Schmid |
| 10,987,468 | B2 | 4/2021 | Mazlish et al. |
| 11,197,964 | B2 | 12/2021 | Sjolund et al. |
| 11,260,169 | B2 | 3/2022 | Estes |

(56) References Cited

U.S. PATENT DOCUMENTS

| | | |
|---|---|---|
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |

(56) References Cited

U.S. PATENT DOCUMENTS

| | | |
|---|---|---|
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birthwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1* | 3/2016 | Schaible ............. A61M 5/1723 |
| | | 604/504 |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1* | 6/2018 | Grosman ............... G16H 20/17 |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1* | 4/2020 | O'Connor ........... A61B 5/4839 |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |

(56) References Cited

FOREIGN PATENT DOCUMENTS

| | | | |
|---|---|---|---|
| EP | 2139382 | A1 | 1/2010 |
| EP | 2397181 | A1 | 12/2011 |
| EP | 2666520 | A1 | 11/2013 |
| EP | 2695573 | A2 | 2/2014 |
| EP | 2830499 | A1 | 2/2015 |
| EP | 2943149 | A1 | 11/2015 |
| EP | 3177344 | A1 | 6/2017 |
| EP | 3314548 | A1 | 5/2018 |
| EP | 1571582 | B1 | 4/2019 |
| EP | 2897071 | B1 | 5/2019 |
| EP | 3607985 | A1 | 2/2020 |
| GB | 2443261 | A | 4/2008 |
| JP | 51125993 | A | 11/1976 |
| JP | 02131777 | A | 5/1990 |
| JP | 2004283378 | A | 10/2007 |
| JP | 2017525451 | A | 9/2017 |
| JP | 2018153569 | A | 10/2018 |
| JP | 2019525276 | A | 9/2019 |
| TW | 200740148 | A | 10/2007 |
| TW | M452390 | U | 5/2013 |
| WO | 9800193 | A1 | 1/1998 |
| WO | 9956803 | A1 | 11/1999 |
| WO | 0030705 | A1 | 6/2000 |
| WO | 200032258 | A1 | 6/2000 |
| WO | 0172354 | A2 | 10/2001 |
| WO | 2002015954 | A1 | 2/2002 |
| WO | 2002043866 | A2 | 6/2002 |
| WO | 2002082990 | A1 | 10/2002 |
| WO | 2003016882 | A1 | 2/2003 |
| WO | 2003039362 | A1 | 5/2003 |
| WO | 2003045233 | A1 | 6/2003 |
| WO | 2004043250 | A1 | 5/2004 |
| WO | 2005110601 | A1 | 5/2004 |
| WO | 2004092715 | A1 | 10/2004 |
| WO | 2005051170 | A2 | 6/2005 |
| WO | 2005082436 | A1 | 9/2005 |
| WO | 2005113036 | A1 | 12/2005 |
| WO | 2006053007 | A2 | 5/2006 |
| WO | 2007064835 | A2 | 6/2007 |
| WO | 2007078937 | A1 | 7/2007 |
| WO | 2008024810 | A2 | 2/2008 |
| WO | 2008029403 | A1 | 3/2008 |
| WO | 2008133702 | A1 | 11/2008 |
| WO | 2009045462 | A1 | 4/2009 |
| WO | 2009049252 | A1 | 4/2009 |
| WO | 2009066287 | A3 | 5/2009 |
| WO | 2009066288 | A1 | 5/2009 |
| WO | 2009098648 | A2 | 8/2009 |
| WO | 2009134380 | A2 | 11/2009 |
| WO | 2010053702 | A1 | 5/2010 |
| WO | 2010132077 | A1 | 11/2010 |
| WO | 2010138848 | A1 | 12/2010 |
| WO | 2010147659 | A2 | 12/2010 |
| WO | 2011095483 | A1 | 8/2011 |
| WO | 2012045667 | A2 | 4/2012 |
| WO | 2012108959 | A1 | 8/2012 |
| WO | 2012134588 | A1 | 10/2012 |
| WO | 2012177353 | A1 | 12/2012 |
| WO | 2012178134 | A2 | 12/2012 |
| WO | 2013078200 | A1 | 5/2013 |
| WO | 2013134486 | A2 | 9/2013 |
| WO | 20130149186 | A1 | 10/2013 |
| WO | 2013177565 | A1 | 11/2013 |
| WO | 2013182321 | A1 | 12/2013 |
| WO | 2014109898 | A1 | 7/2014 |
| WO | 2014110538 | A1 | 7/2014 |
| WO | 2014194183 | A2 | 12/2014 |
| WO | 2015056259 | A1 | 4/2015 |
| WO | 2015061493 | A1 | 4/2015 |
| WO | 2015073211 | A1 | 5/2015 |
| WO | 2015081337 | A2 | 6/2015 |
| WO | 2015187366 | A1 | 12/2015 |
| WO | 2016004088 | A1 | 1/2016 |
| WO | 2016022650 | A1 | 2/2016 |
| WO | 2016041873 | A1 | 3/2016 |
| WO | 2016089702 | A1 | 6/2016 |
| WO | 2016141082 | A1 | 9/2016 |
| WO | 2016161254 | A1 | 10/2016 |
| WO | 2017004278 | A1 | 1/2017 |
| WO | 2017091624 | A1 | 6/2017 |
| WO | 2017105600 | A1 | 6/2017 |
| WO | 2017184988 | A1 | 10/2017 |
| WO | 2017205816 | A1 | 11/2017 |
| WO | 2018009614 | A1 | 1/2018 |
| WO | 2018067748 | A1 | 4/2018 |
| WO | 2018120104 | A1 | 7/2018 |
| WO | 2018136799 | A1 | 7/2018 |
| WO | 2018204568 | A1 | 11/2018 |
| WO | 2019077482 | A1 | 4/2019 |
| WO | 2019094440 | A1 | 5/2019 |
| WO | 2019213493 | A1 | 11/2019 |
| WO | 2019246381 | A1 | 12/2019 |
| WO | 2020081393 | A1 | 4/2020 |
| WO | 2021011738 | A1 | 1/2021 |

OTHER PUBLICATIONS

Unger, Jeff, et al., "Glucose Control in the Hospitalized Patient," Emerg. Med 36(9):12-18 (2004).

"Glucommander FAQ" downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

International Search Report and Written Opinion for the International Patent Application No. PCT/US2021/016283, mailed Jun. 2, 2021, 15 pages.

Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.

Davidson, Paul C., et al., A computer-directed intravenous insulin system shown to be safe, simple,and effective in 120,618 h of operation, Diabetes Care, vol. 28, No. 10, Oct. 2005, pp. 2418-2423.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.

Gorke, A "Microbial Contamination Of Haemodialysis Catheter Connections" Journal of Renal Care, European Dialysis & Transplant Nurses Association.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Schlegel et al, "Multilumen Central Venous Catheters Increase Risk for Catheter-Related Bloodstream Infection: Prospective Surveillance Study" Infection 2008; 36: 322-327.

(56) References Cited

OTHER PUBLICATIONS

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 mailed Jul. 16, 2010.

International Search Report and Written Opinion in PCT/US2008/079641 dated Feb. 25, 2009.

Berger, "Measurement of Analytes in Human Serum and Whole Blood Samples by Near-Infrared Raman Spectroscopy," Ph.D. Thesis, Massachusetts Institute of Technology, Chapter 4, pp. 50-73, 1998.

Berger, "An Enhanced Algorithm for Linear Multivariate Calibration," Analytical Chemistry, vol. 70, No. 3, pp. 623-627, Feb. 1, 1998.

Billman et. al., "Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting"; retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

International Preliminary Report on Patentability for the International Patent Application No. PCT/US2019/053603, mailed Apr. 8, 2021, 9 pages.

International Search Report and Written Opinion for the International Patent Application No. PCT/US2019/053603, mailed Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

Anonymous: "Fuzzy control system", Wikipedia, Jan. 10, 2020. URL: https://en.wikipedia.org/w/index.php?title=Fuzzy_control_system&oldid=935091190.

An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.

International Search Report and Written Opinion for the InternationalPatent Application No. PCT/US2021/017441, mailed May 25, 2021, 12 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, mailed May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, mailed May 27, 2021, 16 pages.

International Search Report and Written Opinion for the International Patent Application No. PCT/US2020/065226, mailed May 31, 2021, 18 pages.

International Search Report and Written Opinion for the International Patent Application No. PCT/US2021/017659, mailed May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (2008, July).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (2001, October).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

(56)        References Cited

OTHER PUBLICATIONS

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on iOS 11", GoToTags, 11 Sep. 2017, web <https://gototags.com/blog/read-hfc-tags-with-an-iphone-app-on-ios-11/> (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

International Search Report and Written Opinion for Application No. PCT/US2019/030562, Sep. 25, 2019, 19 pages.

International Search Report and Written Opinion for the International Patent Application No. PCT/US2020/052125, mailed Aug. 12, 2020, 15 pages.

International Search Report and Written Opinion for the International Patent Application No. PCT/US2020/050332, mailed Sep. 12, 2020, 12 pages.

European Patent Office, "Notification of Transmittal of the ISR and the Written Opinion of the International Searching Authority, or the Declaration," in PCT Application No. PCT/GB2015/050248, Jun. 23, 2015, 12 pages.

International Search Report and Written Opinion for the International Patent Application No. PCT/US2021/012246, mailed Apr. 13, 2021, 15 pages.

International Search Report and Written Opinion for the International Patent Application No. PCT/US2021/013639, mailed Apr. 28, 2021, 14 pages.

International Search Report and Written Opinion for the International Patent Application No. PCT/US2020/063326, mailed May 3, 2021, 17 pages.

European Search Report for the European U.S. Appl. No. 21/168,591, mailed Oct. 13, 2021, 4 pages.

International Search Report and Written Opinion for the International Patent Application No. PCT/US2021/041954, mailed Oct. 25, 2021, 13 pages.

International Search Report and Written Opinion for the International Patent Application No. PCT/US2021/022694, mailed Jun. 25, 2021, 13 pages.

International Search Report and Written Opinion for the International Patent Application No. PCT/US2021/017664, mailed May 26, 2021, 16 pages.

International Search Report and Written Opinion for the International Patent Application No. PCT/US2022/012896, mailed Apr. 22, 2022, 15 pages.

International Search Report and Written Opinion for the International Patent Application No. PCT/US2022/013470, mailed May 6, 2022, 14 pages.

International Search Report and Written Opinion for the International Patent Application No. PCT/US2022/013473, mailed May 6, 2022, 13 pages.

International Search Report and Written Opinion for the International Patent Application No. PCT/US2022/019079, mailed Jun. 2, 2022, 14 pages.

International Search Report and Written Opinion for the International Patent Application No. PCT/US2022/018453, mailed Jun. 2, 2022, 13 pages.

International Search Report and Written Opinion for the International Patent Application No. PCT/US22/018700, mailed Jun. 7, 2022, 13 pages.

International Search Report and Written Opinion for the International Patent Application No. PCT/US22/019080, mailed Jun. 7, 2022, 14 pages.

International Search Report and Written Opinion for the International Patent Application No. PCT/US22/019664, mailed Jun. 7, 2022, 14 pages.

International Search Report and Written Opinion for International Patent Application No. PCT/US2021/051027, mailed on Jan. 7, 2022, 16 pages.

International Search Report and Written Opinion for International Patent Application No. PCT/US2021/052372, mailed Jan. 26, 2022, 15 pages.

International Search Report and Written Opinion for the International Patent Application No. PCT/US2021/046607, mailed Jan. 31, 2022, 20 pages.

International Search Report and Written Opinion for the International Patent Application No. PCT/US2021/055745, mailed Feb. 14, 2022, 13 pages.

International Search Report and Written Opinion for the International Patent Application No. PCT/US21/060618, mailed Mar. 21, 2022, 15 pages.

Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].

Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

International Search Report and Written Opinion for the International Patent Application No. PCT/US2021/052855, mailed Dec. 22, 2021, 11 pages.

International Search Report and Written Opinion for the International Patent Application No. PCT/US2021/047771, mailed Dec. 22, 2021, 11 pages.

Medication Bar Code System Implementation Planning Section I: A Bar Code Primer for Leaders, Aug. 2013.

(56) References Cited

OTHER PUBLICATIONS

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

* cited by examiner

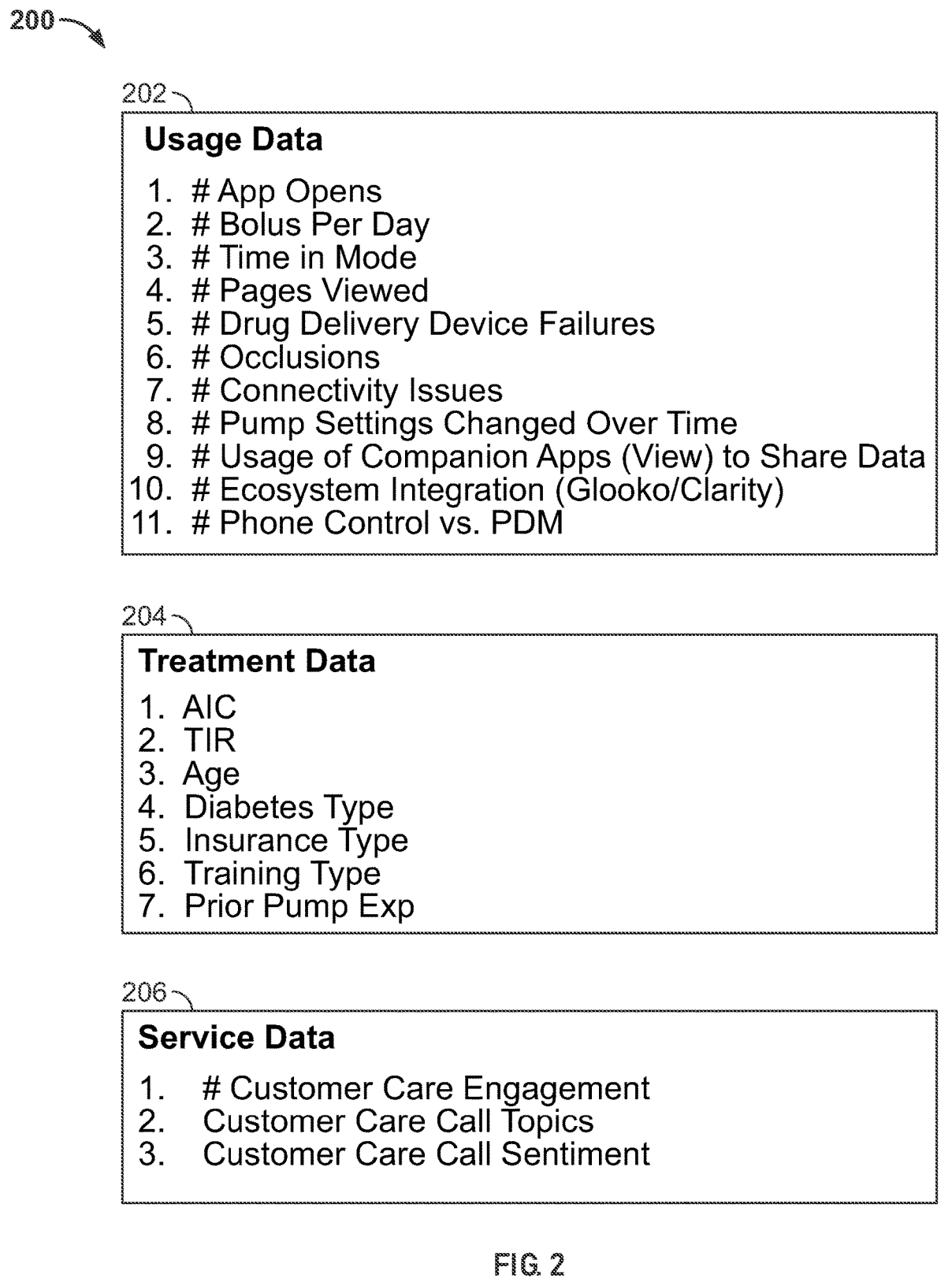

200

202

Usage Data

1. # App Opens
2. # Bolus Per Day
3. # Time in Mode
4. # Pages Viewed
5. # Drug Delivery Device Failures
6. # Occlusions
7. # Connectivity Issues
8. # Pump Settings Changed Over Time
9. # Usage of Companion Apps (View) to Share Data
10. # Ecosystem Integration (Glooko/Clarity)
11. # Phone Control vs. PDM

204

Treatment Data

1. AIC
2. TIR
3. Age
4. Diabetes Type
5. Insurance Type
6. Training Type
7. Prior Pump Exp

206

Service Data

1. # Customer Care Engagement
2. Customer Care Call Topics
3. Customer Care Call Sentiment

FIG. 2

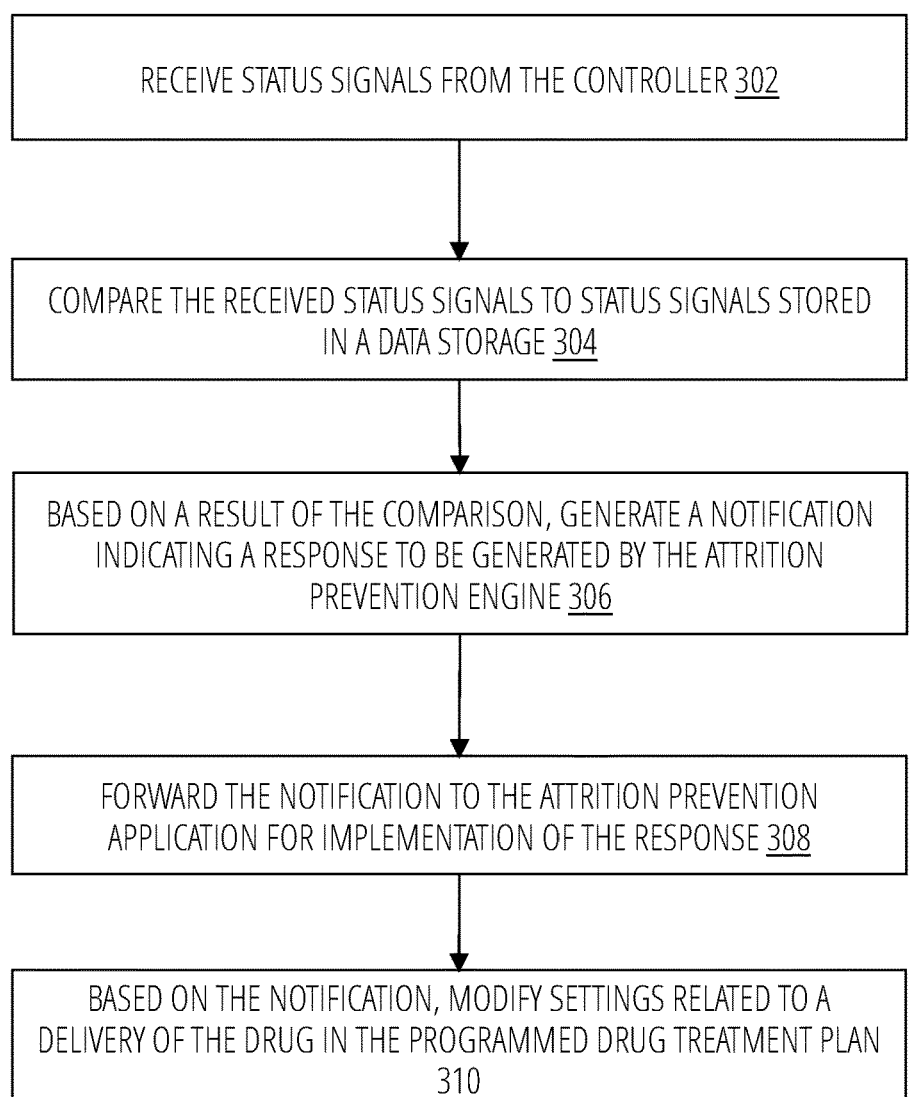

RECEIVE STATUS SIGNALS FROM THE CONTROLLER 302

COMPARE THE RECEIVED STATUS SIGNALS TO STATUS SIGNALS STORED IN A DATA STORAGE 304

BASED ON A RESULT OF THE COMPARISON, GENERATE A NOTIFICATION INDICATING A RESPONSE TO BE GENERATED BY THE ATTRITION PREVENTION ENGINE 306

FORWARD THE NOTIFICATION TO THE ATTRITION PREVENTION APPLICATION FOR IMPLEMENTATION OF THE RESPONSE 308

BASED ON THE NOTIFICATION, MODIFY SETTINGS RELATED TO A DELIVERY OF THE DRUG IN THE PROGRAMMED DRUG TREATMENT PLAN 310

FIG. 3

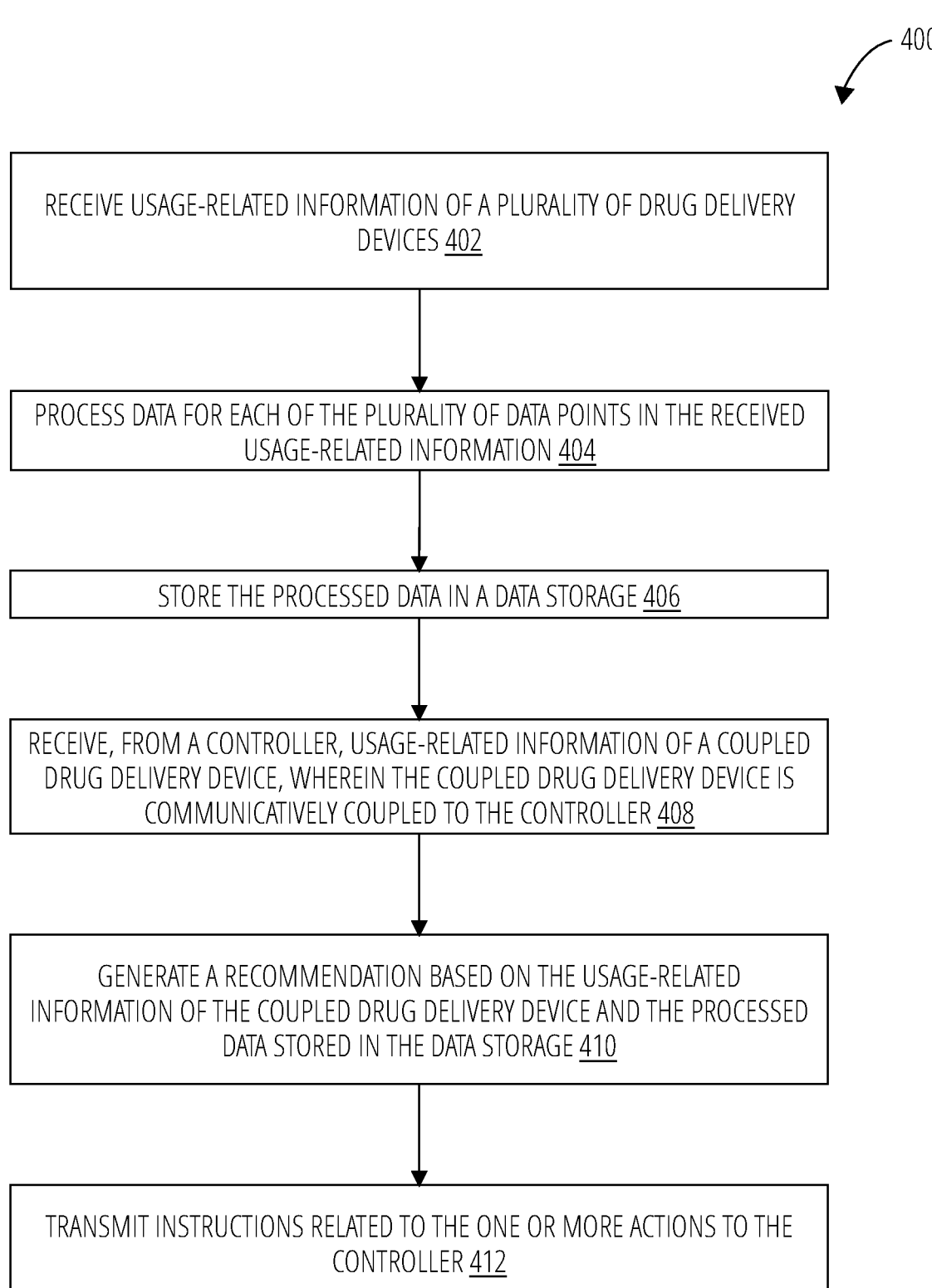

RECEIVE USAGE-RELATED INFORMATION OF A PLURALITY OF DRUG DELIVERY DEVICES 402

PROCESS DATA FOR EACH OF THE PLURALITY OF DATA POINTS IN THE RECEIVED USAGE-RELATED INFORMATION 404

STORE THE PROCESSED DATA IN A DATA STORAGE 406

RECEIVE, FROM A CONTROLLER, USAGE-RELATED INFORMATION OF A COUPLED DRUG DELIVERY DEVICE, WHEREIN THE COUPLED DRUG DELIVERY DEVICE IS COMMUNICATIVELY COUPLED TO THE CONTROLLER 408

GENERATE A RECOMMENDATION BASED ON THE USAGE-RELATED INFORMATION OF THE COUPLED DRUG DELIVERY DEVICE AND THE PROCESSED DATA STORED IN THE DATA STORAGE 410

TRANSMIT INSTRUCTIONS RELATED TO THE ONE OR MORE ACTIONS TO THE CONTROLLER 412

FIG. 4

TECHNIQUES FOR OPTIMIZING USAGE OF AN AUTOMATIC DRUG DELIVERY SYSTEM

RELATED APPLICATIONS

This application claims the benefit of U.S. Provisional Patent Application No. 63/154,164, filed Feb. 26, 2021, the contents of which are incorporated herein by reference in their entirety.

BACKGROUND

Due to the complicated and dynamic nature of the human body's response to drugs, it may be difficult to optimize the use of an automatic drug delivery system. In particular, due to the human body's response to insulin, diabetic users may end up in a hypoglycemic or hyperglycemic state after being treated with insulin therapy. This outcome is undesirable for many reasons: hypoglycemia creates an immediate risk of a severe medical event (such as a seizure, a coma, or a death) while hyperglycemia creates long term negative health effects as well as the risk of ketoacidosis. Whether a person ends up in one of these states depends on a very complicated combination of many factors and sources of error.

Individuals affected with diabetes have a plethora of complicated decisions to make throughout the day to ensure a user is providing themselves with adequate insulin therapy. An automatic insulin delivery system that utilizes an artificial pancreas algorithm or application is operable to make many insulin delivery and insulin therapy-related decisions for a user so that the user can live their lives as close to the average non-diabetic individual as possible. In order to assist users with making the many insulin delivery and insulin therapy-related decisions, the artificial pancreas algorithm may generate alarms and notifications via a personal diabetes management (PDM) device, a wearable drug delivery device, a wearable blood glucose sensor, or other devices, such as accessory devices, that assist with management of a diabetes treatment plan.

People living with diabetes have many options to manage their diabetes. Some decide to use insulin pump therapy, as it can provide better blood sugar control, discretion, and convenience over insulin injections. However, not all users who try pump therapy continue with this therapy. Attrition can be due to several factors and there are several data sources that can help predict which users might terminate insulin pump therapy. Those predictions can also characterize the specific drivers to attrition and be used to make recommended interventions to users and stakeholders (e.g., healthcare provider, customer care, and clinical teams). Targeted recommendations may improve adherence and compliance to insulin pump therapy, which in turn might drive better outcomes for users.

BRIEF SUMMARY

In one aspect, a treatment plan management system includes a drug delivery device operable to deliver a drug to a patient according to a programmed drug treatment plan. The treatment plan management system also includes an analyte sensor operable to measure analytes in blood of the patient and output signals related to analyte measurement values of the measured analytes. The treatment plan management system further includes a controller operable to provide control commands to the drug delivery device, receive inputs from the drug delivery device and the analyte sensor, and execute an attrition prevention application. The treatment plan management system also includes a server communicatively coupled with the controller and a data storage. The server is operable to execute an attrition prevention engine. The server is operable to receive status signals from the controller and compare the received status signals to status signals stored in the data storage. The server, based on a result of the comparison, may generate a notification indicating a response to be generated by the attrition prevention engine, and forward the notification to the attrition prevention application for implementation of the response.

In another aspect, a method is provided that includes receiving status signals from a controller. The status signals include information related to analyte measurement values, information related to delivery of the drug to the patient, and information related to patient interactions with the programmed drug treatment plan. The received status signals may be compared to status signals stored in a data storage. Based on a result of the comparison, a notification indicating a response to be generated by the attrition prevention engine may be generated. The notification may be forwarded to the attrition prevention application for implementation of the response. Based on the notification, settings related to a delivery of the drug in the programmed drug treatment plan may be modified.

In a further aspect, another method provides for receiving usage-related information of a plurality of drug delivery devices, where the received information includes a plurality of data points that are common for each drug delivery device of the plurality of drug delivery devices and fall under categories of usage data, treatment data and service data. The data for each of the plurality of data points in the received information may be processed and the processed data may be stored in a data storage. Usage-related information of a coupled drug delivery device may be received from a controller, and the coupled drug delivery device may be communicatively coupled to the controller. A recommendation based on the usage-related information of the coupled drug delivery device and the processed data stored in the data storage may be generated, where the recommendation includes one or more actions. Instructions related to the one or more actions may be transmitted to the controller, where at least one of the one or more actions includes adjusting operation of the coupled drug delivery device.

BRIEF DESCRIPTION OF THE DRAWINGS

To easily identify the discussion of any particular element or act, the most significant digit or digits in a reference number refer to the figure number in which that element is first introduced.

FIG. 2 illustrates an aspect of the disclosed subject matter in accordance with the disclosed embodiments.

FIG. 3 illustrates a process 300 in accordance with the disclosed embodiments.

FIG. 4 illustrates a process 400 in accordance with another embodiment.

DETAILED DESCRIPTION

Figure 1A:
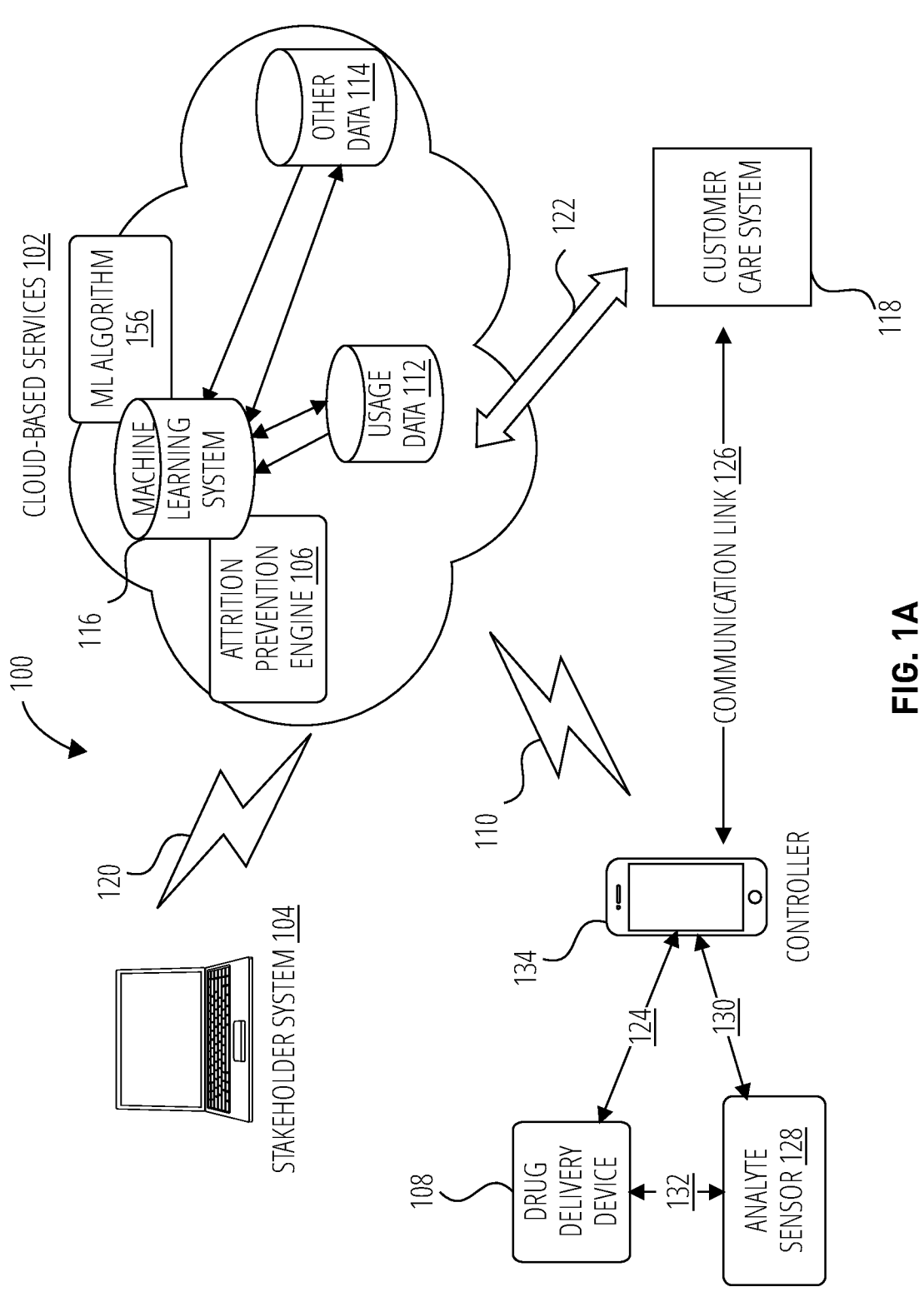
FIG. 1A illustrates an embodiment of a cloud-based services system operable to provide the example processes and techniques described herein.

The examples are described as implemented via a system that utilizes cloud-based services implementing an attrition prevention engine that cooperates with an attrition prevention application executing on a device serving as a patient's controller. The attrition prevention application may be coupled to an artificial pancreas application also executing on the patient's controller.

Predictions of attrition can also characterize the specific drivers to attrition and make recommended interventions to users and/or stakeholders (e.g., health care providers, customer care agents of medical device providers, and clinical teams). By providing targeted recommendation interventions, it is anticipated that there will be improved adherence and compliance to insulin pump therapy (e.g., increased and better use of drug delivery systems) among users, who in turn might experience better outcomes. To those ends, the disclosed embodiments provide an attrition prevention engine, which integrates usage, treatment, and service data, to predict users who have a high likelihood of attrition (based on an attrition prediction algorithm) and to recommend interventions.

An aspect of the disclosed subject matter is the ability to recommend timely intervention methods to reduce user attrition. The recommended interventions can fall broadly into three categories: a) clinical, b) product support, and c) marketing and features. A data science-based approach for the development of metrics and a recommendation for intervention is described.

To improve upon the continued use of a drug delivery device, it would be advantageous if devices, processes, and computer readable media such as those described herein would provide techniques for identifying or determining a probability of attrition setting for a patient. The disclosed examples are processes and devices in which usage-related data is provided to a cloud-based services system that processes the usage-related data. The cloud-based services may implement an attrition prevention engine that may be operable to generate a probability of attrition setting and notifications for the patient whose device provided the usage-related data. The attrition prevention engine in the cloud-based services may work in cooperation with an attrition prevention application that operates on a controller in a drug delivery device system. The controller may control operation of a drug delivery device that is also part of the drug delivery device system. The controller may execute the artificial pancreas application that includes the algorithms for determining drug delivery parameters (e.g., basal dosages, bolus dosages, timing of delivery the basal dosages and the bolus dosages, maximum limits for an amount of drug to be delivered in a day, and the like). In the examples, the attrition prevention application is a computer application that may be a plug-in to the artificial pancreas application and may provide commands that when executed may adjust settings, such as drug delivery settings, user preference settings, and the like. Additionally, or alternatively, the attrition prevention application may cause the artificial pancreas application to adjust the settings.

FIG. 1A illustrates an example of a system operable to provide the example processes and techniques described herein. The system 100 may include cloud-based services 102, a controller 134, a stakeholder system 104 and a customer care system 118.

Cloud-based services 102 may be provided by an enterprise, such as a health care product provider. The cloud-based services 102 may include an attrition prevention engine 106, machine learning system 116, and data stores (also referred to as a data lake) usage data 112 and other data 114. The cloud-based services 102 may be configured with communication interfaces (not shown) that enable access via communication links, such as wireless communication links 110 and 120, with respective devices and systems, such as controller 134 and stakeholder system 104. In addition, the cloud-based services 102 may couple to and communicate with other systems in, or associated with, the enterprise, such as customer care system 118, via a communication link 122.

In some embodiments, the attrition prevention engine 106 may be programming instructions embodied in a non-transitory computer readable medium. In other embodiments, the attrition prevention engine 106 may be a server that executes programming instructions that evaluate status signals obtained from the controller 134 and the drug delivery device 108 and provides recommendations in the form of notifications based on the results of the evaluation. The recommendations are based on data analysis that has been shown to mitigate the reasons (e.g., difficulty in use or setup, device failures, inappropriate automatic drug delivery settings, and the like) for a patient not realizing the full capabilities of an automatic drug delivery system in a manner consistent with the patient's lifestyle.

The stakeholder system 104 may be a computer system or computer environment of a healthcare provider, a healthcare provider network or system, or a guardian of a patient, or the like. The stakeholder system 104 may be operable to provide data, such as usage data 112 or other data 114, to the attrition prevention engine 106.

The controller 134 may be a computerized device, such as a smartphone or the like, that is operable to control a drug delivery device 108. The drug delivery device 108 that may cooperate with the controller 134 may be a wearable drug delivery device or may be a tube or pen-like drug delivery device. The controller 134 and the drug delivery device 108 may be associated with a patient (e.g., a patient account associated with data from the controller 134 and drug delivery device). For example, the patient may be enrolled with cloud-based services 102 to receive assistance with the use and management of the drug delivery device 108 as well as the use and the functions of the controller 134 so the patient may optimize use of both which in turn optimizes the management of the patient's disease, such as diabetes.

The controller 134 is operable to communicate with drug delivery device 108 via communication link 124. The communication link 124 may be a wired or wireless communication link. Via the communication link 124, the controller 134 may deliver command signals that instruct the drug delivery device 108 how to operate and may receive status signals from the drug delivery device 108. For example, the command signals sent to the drug delivery device 108 may instruct the drug delivery device 108 to deliver a dose of a drug at a particular time or instruct the drug delivery device 108 to modify a pending drug delivery or a drug delivery setting (such as a maximum drug dosage limit). The status signals received from the drug delivery device 108 by the controller 134 may be status signals related to an amount of the drug that was most recently delivered, a list of alarms or notifications related to different components and systems of the drug delivery device 108, and the like. The controller 134 may also receive measurement values from an analyte sensor 128. The analyte sensor 128 may be operable to measure an analyte in the blood or a body of a patient, such as blood glucose. For example, the analyte sensor 128 may be a blood glucose detector operable to measure blood glucose and an analyte measurement value is a blood glucose measurement value.

In an example, the analyte sensor 128 may include a transceiver operable to wirelessly communicate with the drug delivery device 108 and other devices. The analyte sensor 128 may include one or more detectors respectively operable to measure parameters related to one or more analytes of the patient, and logic circuitry (e.g., a processor) coupled to the transceiver and the one or more detectors, the logic circuitry operable to control the analyte sensor and the transceiver. Other technical features may be readily apparent to one skilled in the art from the following figures, descriptions, and claims. The analyte sensor 128 may report, for example, the blood glucose measurement values to the controller 134 via communication link 130 and to the drug delivery device 108 via communication link 132. The communication links 124 and 130 may be, for example, Bluetooth links established according to the Bluetooth protocol.

An example of establishing communication between the controller 134 and the drug delivery device 108 is described in more detail with reference to FIG. 1B.

In an example of the system 100, the attrition prevention engine 106 in the cloud-based services 102 may perform the tasks of monitoring, measuring, recommending and processing feedback. When monitoring, the attrition prevention engine 106 may process data provided by the controller 134 that includes the data provided by the drug delivery device 108 and the analyte sensor 128. For example, usage, treatment, and service data contain the crucial variables used to drive an attrition prediction algorithm executed by the attrition prevention engine 106 as well as attrition prevention application 150. As shown in FIG. 1A, usage data sent from the user's cloud-connect devices are stored on an internal data lake that includes usage data 112 and other data 114. Treatment, customer service, and other types of data may be also stored within the data lake using other database and structured (or semi-structured) data sources (e.g., a commercial database). An example of the set of data collected is shown in and described with reference to FIG. 2 may be used for the attrition prediction algorithm.

Usage data may be collected from the drug delivery device 108 as well as applications, such as a medication delivery application (MDA) (described with reference to FIG. 1B) on the controller 134. At different times, such as periodically or after an event (e.g., a bolus), or continuously, the collected usage data may be sent from the controller 134 to the cloud-based services 102 for storage in the usage data 112 data store.

When the crucial usage-related data is in the data stores (also referred to as a data lake), such as the usage data 112 and other data 114, the attrition prevention engine 106 may measure the respective data and process the data and the measurements to analyze attrition and calculate attrition probabilities for the patient. The usage data 112 may be used to drive a machine learning (ML) algorithm in machine learning system 116. Examples of data stored as usage data in the usage data 112 data store is described with reference to FIG. 2.

The ML algorithm (e.g., a logistic regression function, XGBoost, or the like) may use the data as predictor variables in order to produce a probability value that represents a probability of patient attrition (i.e., a user's likelihood to abandon use of the drug delivery device). Attrition may be modeled using the same usage data and user-based data obtained from other patients that choose to share their usage data and other data. Attrition may be defined, for example, as infrequent application opens and drug delivery device activations (among others). Once the ML algorithm 156 has generated a probability for any given user, the probability is fed back into the data lake to be stored with the other data 114 data storage.

In parallel, a recommendation is generated via the ML algorithm 156 as executed by the machine learning system 116 based on the factors that contributed most to the attrition probability. Recommendations are triggered within the database based on logic associated with monitoring the database and the recommendations are sent to the user and Stakeholder system 104, such as a healthcare professional, a customer care system 118, a guardian of the patient, and the like. The recommendation may also be stored in the data lake as other data 114. Examples of data stored as other data in the other data 114 data store is described with reference to FIG. 2.

Once the attrition probability and recommendation are stored within the data lake, the ML algorithm 156 is operable to trigger alarms to implement various interventions. The attrition probability may cause ML algorithm 156 to generate different responses. For example, a lower attrition probability may cause the generation of an automated response, while a higher attrition probability may cause the ML algorithm 156 to initiate human interaction. For example, a user with a relatively low attrition probability may get a push notification in their cloud-connected diabetes management device. The push notification may encourage a patient to try out new features via controller 134, provide usage tips for both the drug delivery device 108 and the controller 134, or recommend help resources (such as websites, videos, or in-person assistance from a customer care system 118). Alternatively, for a user with a high attrition probability, the in-person assistance from the customer care system 118 initiated by the ML algorithm 156 may include a member of a clinical team reaching out (e.g., calling, emailing, texting, or sending a notification, for example) to the patient to better understand the issues and help with any issues a patient may be having with the drug delivery device 108, controller 134 or another part of the system.

Another aspect of the attrition prevention engine 106 is the feedback obtained from the data fields within the data stores usage data 112 and other data 114, which are updated based on interactions (either via the controller 134 or the customer care system 118) with the patient. The feedback (represented by the two-way arrows) enables the attrition prediction ML algorithm 156 executed by the attrition prevention engine 106 to be updated.

The post-intervention user-based data (from other users' devices and other stakeholders) can be used to further refine the recommendations, update the attrition probabilities, and provide feedback and training to the ML algorithm 156. Furthermore, common intervention patterns over time can spawn new internal programs that address common large-scale drivers to attrition (including product design, training, etc.).

The common large-scale drivers to attrition may be modeled in different ways. The respective attrition models may be built on features that include clinical outcomes, product settings, user behavior and product performance. Again, machine learning algorithms or tools, such as logistic regression, XGBoost, support vector machines and decision trees, may provide model framework for the attrition and intervention models. Examples of each of these models are described below with reference to FIGS. 5-8B.

In an operational example, the attrition prevention engine 106 when configured as a server may receive status signals from the controller 134. In the example, the status signals may include usage information related to analyte measurement values, information related to delivery of the drug to the patient, information related to patient interactions with the programmed drug treatment plan, or the like. Further examples of the information included in the status signals is described with reference to FIG. 2. The attrition prevention engine 106 may compare the received status signals to status signals stored in the data storage, such as usage data 112 and other data 114. Patterns of usage by other users of automatic drug delivery systems (e.g., daily use, sporadic use, rigid implementation of recommended use, lackadaisical implementation of recommended use, or the like) and their outcomes, i.e., continued use of a drug delivery device or abandoned use of a drug delivery device, may be maintained as other data 114. A server implementing the attrition prevention engine 106 may be operable, based on a result of the comparison, to generate a notification indicating a response to the information in the received status signals. The attrition prevention engine 106 may forward the notification to an application executing on the controller 134, such as attrition prevention application 150, for implementation of the response. Additional details are provided with reference to the process discussion of FIGS. 3-8B.

Figure 1B:
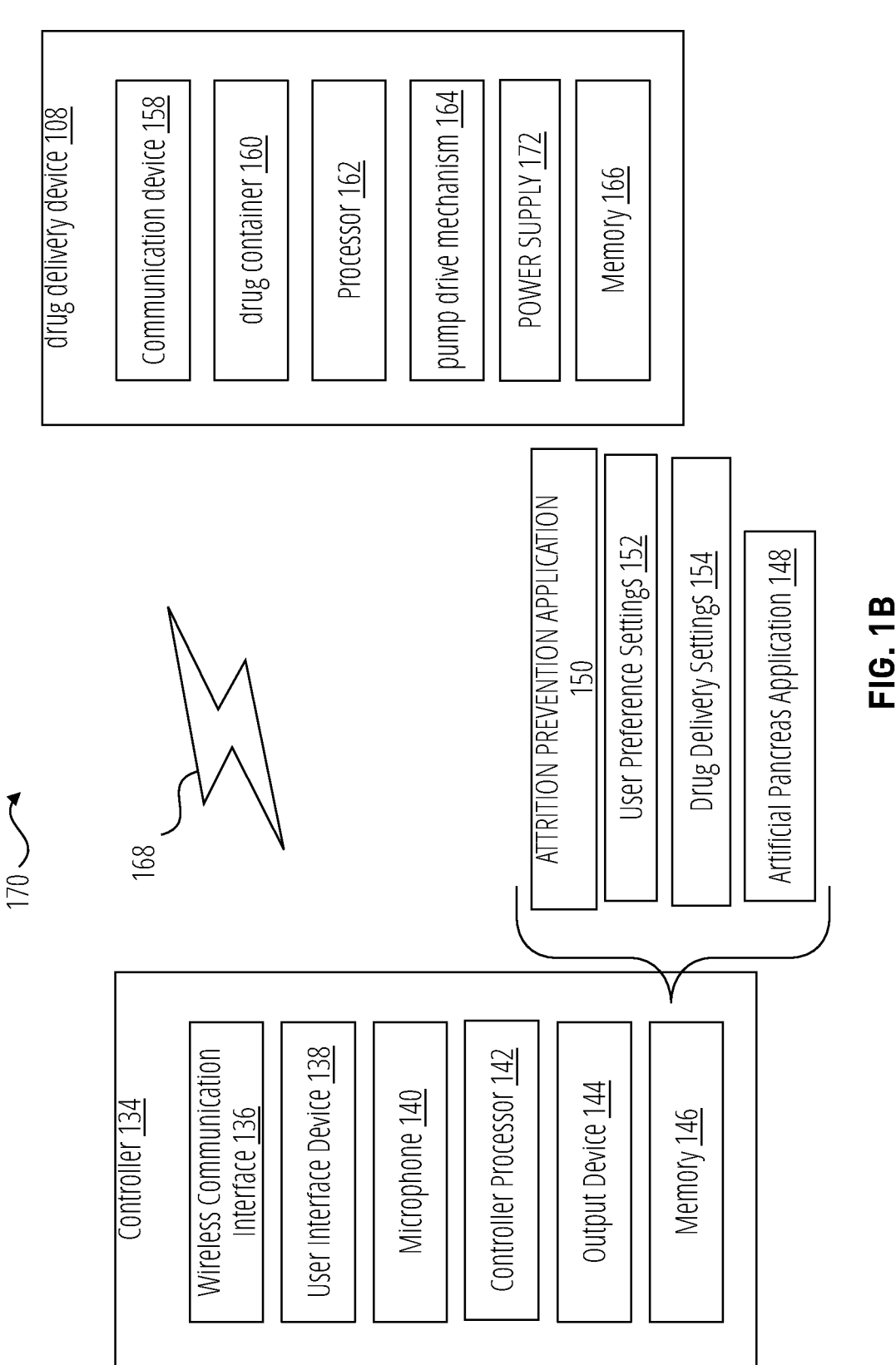
FIG. 1B illustrates an embodiment of a drug delivery system operable to work within the cloud-based services system of FIG. 1A and to provide the example processes and techniques described herein.

FIG. 1B illustrates an example of a drug delivery system operable to work within the cloud-based services system of FIG. 1A and to provide the example processes and techniques described herein. The drug delivery system 170 may include the controller 134 and the drug delivery device 108.

The controller 134 may be operable as a drug treatment management device and may have a controller processor 142, a memory 146, a wireless communication interface 136, and a user interface device 138. The controller 134 may be a smartphone that executes a computer application such as the artificial pancreas application 148 and the attrition prevention application 150.

The user interface device 138 may be buttons coupled to a display, a touchscreen display, or the like that enables a user to interact with/and adjust user preference settings 152 as well as other settings. In one or more examples, the controller 134 may have an output device 144 (such as a speaker, a vibration mechanism, a light or the like), a microphone 140, a user interface device 138, and the like. In an example, the memory 146 may be coupled to the controller processor 142 and be operable to store programming code and computer applications. The computer applications stored in the memory 146 may include a medication delivery application, such an artificial pancreas (AP) application 148, and other computer applications that, for example, may support implementation of medication management plan, such as a diabetes treatment plan. The memory 146 may also store user preference settings 152 and drug delivery Settings 154. User preference settings 152 may for example be settings that indicate how the controller 134 should notify the patient of alarms and the like, volume of notification indicators, mealtimes, sleep times, and the like. Drug delivery settings 154 may be settings such as a maximum daily amount of the drug to deliver, a drug sensitivity setting, connectivity setting and the like.

The attrition prevention application 150 executing on the controller processor 142 may configure the controller 134 to communicate with a customer care system, such as customer care system 118 of FIG. 1A, via a communication link.

The artificial pancreas application 148 may, for example, incorporate programming code that provides functionality for managing the patient's diabetes according to a drug treatment plan. The artificial pancreas application 148 may be communicatively coupled to another computer application, such as the attrition prevention application 150, that operate in cooperation to provide the functionality described in the examples such as monitoring, measuring, providing feedback, or recommending, as well as other functions as described herein.

In an example, the controller processor 142 may be operable to establish a connection with one or more of the cloud-based services 102 of FIG. 1A. For example, the wireless communication interface 136 may be a Bluetooth® transceiver, or a transceiver operable according to IEEE 802.11 family of communication protocols or a cellular transceiver, and may be operable to establish, under control of the controller processor 142, a wireless communication link, such as 126 with a paired with the controller 134. For example, the artificial pancreas application, via the processor 142, may request via the wireless communication interface 136 a pairing with the controller 134 of FIG. 1. The pairing request may include an authentication code that indicates to the drug delivery device 108 that the request is from a verified device. In response to the pairing request, a wireless communication link 126 may be established with the drug delivery device 108, which is now a paired device, for receipt of instructions from the controller processor 144 as well as transfer of usage information, such as drug delivery information (e.g., basal doses and/or bolus doses), alarms/notifications, and the like.

In a further example as explained with reference to both FIGS. 1A and 1B, the artificial pancreas application 150 is operable to communicatively coupled, via the wireless communication interface 138, to an analyte sensor 128 in FIG. 1A. The analyte sensor 128, which may be a continuous blood glucose sensor that provides periodic measurements of blood glucose or a blood glucose meter that the patient may manually operate. The blood glucose measurements are received as blood glucose measurement values. The controller processor 142 may be operable to receive the blood glucose measurement values from the analyte sensor 128 in FIG. 1A via a wireless communication link 130 established with the wireless communication interface 138. For example, the artificial pancreas application 150 may be operable to determine basal doses and/or bolus doses based on the received blood glucose measurement values and the drug delivery settings 156, which may also include user preference settings 152. In addition, based on the drug delivery settings 156, the artificial pancreas application 150 may determine drug delivery doses and dosages including basal doses and bolus doses. Additionally, the attrition prevention application 150 may be operable to receive a notification from the attrition prevention engine 106 indicating a response to the information in the received status signals.

For example, when notifications are received from the attrition prevention engine, prompts generated based on the notifications may be presented by the attrition prevention application 152 via an output device 144 or the user device interface 138. For example, the output device 144 may be a speaker communicatively coupled to the artificial pancreas application 150 executing on the controller processor 144 or the output device 144 may be a touchscreen. The artificial pancreas application 148 or the attrition prevention application 150 also executing on the controller processor 144 may format the outputted notification or the outputted prompt as synthesized speech, a sound or a presentation on a touchscreen or display, when the user interface device 138 is a touchscreen or a display.

The drug delivery device 108 may be physically coupled to a patient via an adhesive or the like and provide a drug, such as insulin, glucagon, a glucagon-like peptide, and/or another drug from the drug container 160, to the patient in response to commands received via the artificial pancreas application 148. The controller processor 142 may obtain from a drug delivery device 108, information regarding status of the controller 134, an indication of successful delivery of the drug to the patient, or other information. In at least one embodiment, the drug delivery device 108 may be a wearable drug delivery device or a tube or pen-like drug delivery device.

The drug delivery device system 170 may include a controller 134 and a drug delivery device 108. The drug delivery device 108 of the drug delivery system 170 may include a processor 162, a memory 166 storing programming code executable by the processor 162, a drug container 160 (also referred to as the drug reservoir or reservoir component) operable to contain a liquid drug, a pump drive mechanism 164 (also referred to as a pump drive or pump system) operable to expel the liquid drug from the drug delivery device, and a communication device 158 coupled to the processor 162 and operable to wirelessly communicate with one or more devices, such as controller 134 and analyte sensor 128 of FIG. 1A. Examples of the liquid drug may include pain relievers, diabetes medications (e.g., insulin, glucagon, glucagon-like peptide or the like), chemotherapy drugs, hormones and the like.

The processor 162 of the drug delivery device 108 may implement logic to detect operational features, such as occlusions (i.e., blockages in a fluid path between the reservoir and a subcutaneous region of the patient's skin), connectivity issues, drug delivery device failures, a number of user interactions with the drug delivery device 108, and the like. The processor 162 may use communication device 158 to transmit data related to the operational features to the controller 134 for evaluation or transmission to the attrition prevention engine 106 of FIG. 1A. The processor 162 may be operable when executing the programming code to establish a wireless communication link 168 via the communication device 158 with the controller 134. The processor 162 may receive, via a wireless communication link, such as 132 of FIG. 1A, measurement values obtained by and output from a detector in the analyte sensor 128 of FIG. 1A.

In an example, the controller processor 142 is operable to output to the user interface device 138 a user notification with resource information, receive via the user interface device, a selection of a contact within the resource information. In response to the selection, the controller may implement a communication session via the communication device, and based on the results of the communication session, drug delivery settings of the drug delivery device may be modified. The modified drug delivery settings may be selected based on a likelihood of achieving a patient's target blood glucose levels and improving the patient's time in range.

The controller processor 142 may be further operable, by execution of the artificial pancreas application 148 or the attrition prevention application 150, or both, to adjust basal rate doses or bolus doses of the drug delivery to the patient, and based on the results of the communication session, modify drug delivery settings 154 of the drug delivery device 108. Alternatively, or additionally, the controller processor 142 may be further operable to determine a basal rate dose that given information obtained from the received status signals is intended to achieve a target blood glucose level for the patient. The determined basal rate dose is also intended to increase an amount of time in range of the target blood glucose level. The controller processor 142 causes delivery of the determined basal rate dose when controlling the drug delivery device according to the modified drug delivery settings.

An example of a process implemented by a computer application, such as attrition prevention application 150, is described in more detail with reference to FIGS. 3-8B.

A subset of the data 200 collected and used for the attrition prediction ML algorithm/model may include usage data 202, treatment data 204 and service data 206 as shown in FIG. 2. The attrition prevention engine, such as attrition prevention engine 106 in FIG. 1A, may use other databases and (semi-)structured data sources, such as commercially available database systems to store and manage the various forms of data. The usage, treatment, service, and other types of data 200 may be stored within the data lake or data stores of the cloud-based services referenced in FIGS. 1A and 1B.

For example, with reference to FIGS. 1A and 1B, an attrition prevention application 150 operating on the controller 134 may collect usage data 202 from a medication delivery application, such as artificial pancreas application 148. The artificial pancreas application 148 executing on the controller may receive data from the drug delivery device. In addition, or alternatively, the controller 134 may store data derived from commands generated by the artificial pancreas application 148 from the usage data 202.

Examples of the usage data 202 as shown in FIG. 2 include, for example, the number of times a patient opened the artificial pancreas application 148, the number of bolus doses delivered per day, the amount of time a user spent in each mode (i.e., time in mode) of the drug delivery device, a number of pages viewed, a number of delivery device failures, a number of detected occlusions, a number of connectivity issues, a number of pump settings changed over time, a number of views of a companion application (e.g., Glooko, or the like) in which data was shared, ecosystem integration, and phone control versus dedicated controller (e.g., personal diabetes management device). Of course, other data may also be included in the usage data, such a battery power levels, pump cycles and the like. In addition, less data may be used but the decreased granularity may negatively affect the output of the attrition prediction engine.

The drug delivery device has a number of possible modes, and the times when the mode changes are recorded. The duration between changing into a mode and subsequently changing to a different mode is the time spent in that mode. The total duration for each mode over a time period (hour, day, week, etc.) may be summed, and the result expressed as the numerical value of the sum, or as the fraction of time spent in that mode (e.g., the value of the sum divided by one hour, day, week, etc.)

Example of treatment data 204 may include A1C (also referred to as HbA1C), time in range (TIR), patient's age, patient's weight, patient's gender, diabetes type, insurance type, an amount, timing, and depth of training (e.g., training type), a patient's prior pump experience (e.g., months or years), and the like.

Example of service data 206 is related to a number of times a patient engaged with customer care, the customer care topics the patient discussed or requested information about when engaging with customer care, and the customer care engagement sentiment.

FIG. 3 illustrates a process 300 in accordance with one embodiment. A server executing the attrition prevention engine 106 may implement the process 300. As process 300 is implemented, the attrition prevention engine may receive, at block 302, status signals from a controller, such as controller 134. As described with reference to FIGS. 1A and 1B, an attrition prevention application may be executing on the controller. The attrition prevention application may receive status signals that enable collection of information related to the drug delivery device and signals. The status signals may, for example, include information related to analyte measurement values, information related to delivery of the drug to the patient, information related to patient interactions with the programmed drug treatment plan, and the like.

In one aspect of block 302, previous status signals that indicated retention of the patient as a user of the drug delivery device as well as other previous status signals that indicated attrition of the patient from further use of the drug delivery device may be stored in a database, such as other data 114. The database may, for example, be continuously updated with status signals and with the disposition of the patient corresponding to the respective status signals. For example, an attrition prevention engine of the cloud-based services may analyze the received status signals and determine the received status signals may include data consistent with regular usage, such as consistent delivery of drugs, time in range, few calls to customer care or frequent calls confirming advanced usage techniques (e.g., requesting information about more automatic drug delivery settings) and the like. In such a case, the received status signals indicate the patient is continuing to use the drug delivery device (e.g., a retained user). When the patient is identified as a retained user, the received status signals may be flagged with a corresponding disposition setting of "retention" or "retained." Conversely, the attrition prevention engine may analyze the received status signals and determine the received signals indicate a patient is no longer using the drug delivery device (e.g., an abandoned user) because the received status signals indicate reduced time in range, frequent application openings, frequent pump settings and many calls (i.e., engagements) with customer care, multiple drug delivery device failures or other indicators of difficulty with the drug delivery device. In this case, the received status signals may be flagged by the attrition prevention engine with a corresponding disposition setting of "attrition" or "attrited." in the database.

In block 304, the attrition prevention engine implementing the process 300 may compare the received status signals to status signals stored in the data storage. The status signal stored in the data storage may be previously-received status signals. Based on the results of the comparison, in block 306, the attrition prevention engine may generate a notification to be delivered to the controller. For example, when the comparison results in a match between stored status signals (with a disposition) and received signals, the attrition prevention engine generates the notification, which may include a recommendation for actions to be taken by the attrition prevention application executing on the controller to assist the patient with optimizing the use of their drug delivery device according to the patient's preferences, programmed drug treatment plan, and the drug delivery device capabilities.

In block 308, the process 300 may cause the server to forward the notification to the attrition prevention application for implementation of the response included in the recommendation. The server may transmit the notification via different messaging platforms or protocols, such as email, short messaging service (SMS), multimedia messaging service (MMS), rich communication services (RCS), and the like over different networks, such as cellular data, WiFi, Bluetooth, and the like. The notification may indicate a response to implemented by attrition prevention application executing on the controller. The response indicated in the notification may be instructions for the attrition prevention application to execute. The instructions may be for the attrition prevention application to generate a prompt with preset text informing the patient of actions the patient may take to optimize the use of their drug delivery device, modifications to drug delivery dosages and times as controlled by the artificial pancreas application, and the like. More detailed examples of the instructions and resulting actions are described below with reference to examples shown in FIGS. 5-8B that are based on a type of model used to evaluate the received status signals.

In block 310, the attrition prevention application according to process 300 may, based on the notification, modify settings related to a delivery of the drug in the programmed drug treatment plan. For example, the notification may include instructions to a controller indicating modifications to drug delivery settings of the drug delivery device controlled by the controller. The drug delivery settings may include drug dosage amounts and timing of the dosages. In response to the notification (and the included instructions, the attrition prevention application may cause the controller to output an actuation signal to be delivered to a pump mechanism of the drug delivery device. The actuation signal may indicate a drug dosage (and perhaps a time, if the drug dosage is not to be delivered immediately) that is based on the modified settings.

After delivery of the notification, the attrition prevention application may generate a request for additional details. The attrition prevention engine may receive the request for details of the indicated response from the controller and provide the details of the indicated response back to the controller. For example, the notification may indicate resources (e.g., article on use of a particular feature, such as a bolus calculator, of the controller and the drug delivery device) for the patient to review, the attrition prevention application may send a request for the link or a file containing a copy of the article.

Another process that may be implemented is described in more detail with reference to FIG. 4.

In block 402, process 400 may receive usage-related information of a plurality of drug delivery devices. In the process 400, the received information may include a plurality of data points that are common, or the same, for each drug delivery device of the plurality of drug delivery devices. The plurality of data points may fall under categories of usage data, treatment data and service data.

In block 404, process 400 may process the received data for each of the plurality of data points in the received information. The received data may be processed according to one or more models that produce recommendations to assist users or patients in continued use of the drug delivery device and mitigate attrition among patients away from use of the drug delivery device. The processing of the data in block 404 may be according to one or more models that evaluate the features of the processed differently to provide different recommendations. Examples of the one or more models are explained with reference to FIGS. 5-8B.

The process 400 as shown in block 406 may store the processed data in a data storage. For example, the processed data may be stored in a data lake or data storage that includes clinical data, usage data, such as usage data 112 of FIG. 1, and other data, such as 114 of FIG. 1.

In block 408, the processor executing the process 400 may receive, from a controller, usage-related information of a drug delivery device that is communicatively coupled to the controller. The received usage-related information may include a plurality of data points that are the same data points, or several common data points, for each drug delivery device of the plurality of drug delivery devices. The plurality of data points may fall under categories of usage data, treatment data and service data, or the like.

In block 410, process 400 generate a recommendation based on the usage-related information of the coupled drug delivery device and the processed data stored in the data storage.

In block 412, execution of process 400 may include transmitting instructions related to the one or more actions to be taken the controller. The transmitted instructions may be interpreted by an attrition prevention application executing on the controller. The one or more actions to be taken by the controller as commanded by the attrition prevention application may include, for example, adjusting operating parameters of the coupled drug delivery device. The adjustment of the operating parameters may include, for example, modifying drug delivery doses and delivery time schedules in a health management plan or a drug treatment plan of the patient.

An example of a model that may be used to process the usage-related data as well as the other data collected by the attrition prevention engine with respect to treatment and service data is a clinical outcome model. The premise of the clinical outcome model is based on controlling blood glucose. A principal measure of blood glucose control is time in range (TIR), which may be a percentage of blood sugar readings that are above a lower bounding value (typically 70 mg/dl) and below an upper bounding value (typically 180 mg/dl). A patient is more likely to attrite if their TIR is poorly maintained. Historical attrition data, such as the previously-received status signals and a corresponding disposition, may be stored, for example, in the usage data 112 or other data 114 of FIG. 1 and may be used to determine a probability of attrition setting.

Figure 5:
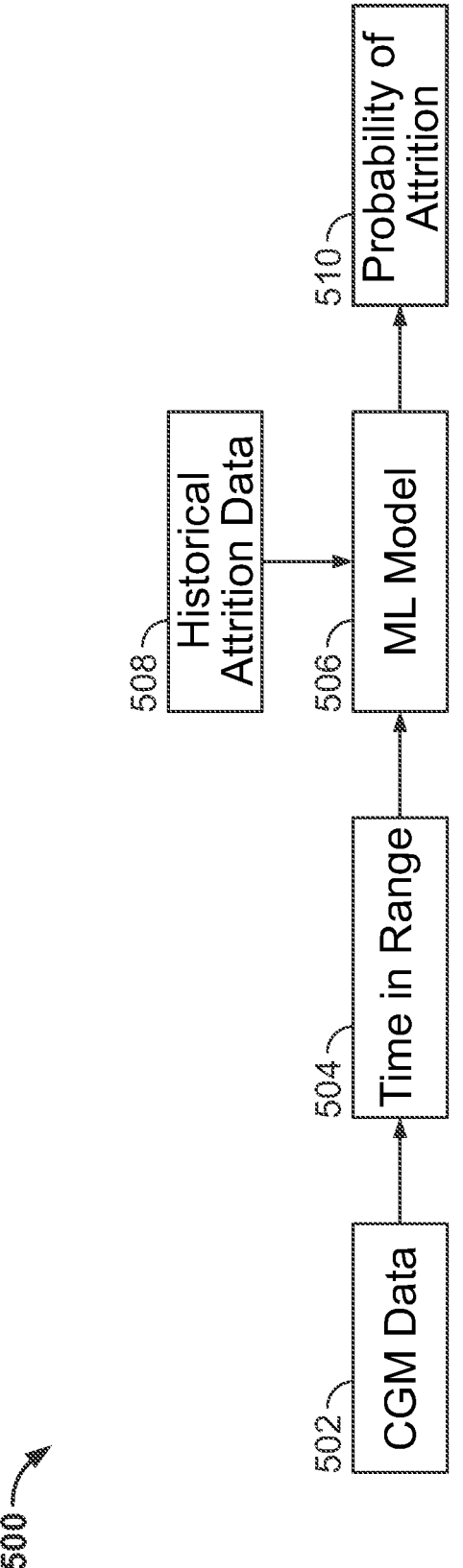
FIG. 5 illustrates an aspect of the subject matter in accordance with the disclosed embodiments.

An operational example of the application of the clinical outcome model to the usage-related data is described with reference to clinical model 500 of FIG. 5. In the use of the clinical model 500 of FIG. 5, the continuous glucose monitor (CGM) data 502 may be evaluated by the attrition prevention application executing on the controller. The attrition prevention application may be operable to extract a TIR value 504 from the CGM data 502 or may determine the TIR value 504 based on an analysis of the CGM data 502. Alternatively, or in addition, the controller may forward the CGM data 502 as treatment data within the usage-related data provided to attrition prevention engine in the cloud-based services.

The clinical outcome model 500 may be implemented as a machine learning model 506. The machine learning model 506 may be a machine learning algorithm, such as ML algorithm 156, that is implemented by machine learning system 116. The machine learning system 116 may use the TIR value 504 received from the attrition prevention engine as an input into a machine learning (ML) model 506 that has been trained using historical attrition data 508. The historical attrition data 508 may be data obtained from users that are confirmed as abandoning (or attriting) the use of a drug delivery device but may also include data obtained from users that have continued to use the drug delivery device.

The ML model 506 may have weightings and settings that enable evaluation of the inputs and output of a probability of attrition 510. In an example, weightings and settings are determined by training the ML model on historical data. The trained data is then applied to new data, yielding predictions for that new data. It is desirable to use as much data as is available and relevant. Some aspects of the data may change with new devices (e.g., some data from earlier drug delivery devices and control devices may not be relevant for newer drug delivery devices and newer control devices). Other data always remains relevant, such as that relating specifically to diabetes rather than relating to treatment using a specific device. Three years and 100,000 users are reasonable numbers to include as weights and settings.

The ML model 506 may generate one of a number, such as three, of probability of attrition settings based on a time in range percentage. For example, the ML model 506 may determine the probability of attrition setting as a low probability when a time in range percentage is greater than or equal to 70 percent (i.e., IF TIR>70% THEN probability of attrition is LOW); a medium probability setting when a time in range percentage is less than 70 percent but greater than 50 percent (i.e., IF 50%<TIR<70 THEN probability of attrition is MEDIUM); and a high probability setting when a time in range percentage is less than 50 percent (i.e., IF TIR<40% THEN probability of attrition is HIGH). In response to the determination of a probability of attrition, the ML model 506 may output the set probability of attrition 510 for further evaluation in determining a notification, instructions and a recommendation to be delivered to the controller.

An example of when a rule triggers a low or medium probability of attrition setting based on the TIR determination. The attrition prevention engine (APE) may notify a clinical team to reach out to follow up with the patient. In addition, the APE may send an alert to the patient's health care provider (who has the patient's permission to be notified) via email and is provided a view of the patient's blood glucose value history with other relevant data. The patient, in addition to being contacted by the clinical team, may also be notified with statistics related to TIR/percentage of time high (e.g., amount of time blood glucose is over target)/percentage of time low (e.g., amount of time blood glucose is below target), suggestions on how to improve, and resource information including customer care and health care provider contact information, and links to websites and videos. In addition to alerting the patient, the APE may be operable as part of an artificial pancreas application/algorithm to adjust basal rates/bolusing of drugs delivered to the patient to achieve target blood glucose levels as well as improving the patient's time in range. A more consistent time in range has been indicated as a reason for reduced attrition.

An example of high probability of attrition setting may be TIR below 40% or the like. The response to the high probability of attrition setting from the clinical outcome model executed by the APE may include the clinical team, which is part of the customer care team, may be notified to urgently reach out as a follow up with the patient. In addition, the patient's health care provider (who has the patient's permission to be notified) may be sent an alert via email or other messaging service and may be provided with a view of the patient's blood glucose value history with other relevant data. In addition, or alternatively, the healthcare provider may also be contacted by telephone by a clinical team member of the customer care team. The patient may also be notified via email or SMS/MMS with information and statistics related to TIR/percentage of time being higher than target (e.g., a percentage indication of an amount of time the blood glucose was over target), the percentage of time the blood glucose was low (e.g., a percentage indication of an amount of time blood glucose is below target), suggestions on how to improve the time in range, and resource information including customer care and health care provider contact information, and links to websites and videos. The information may also be sent by home delivery mail or the like. In addition, the APE when a determination is made that the probability of attrition is high due to the TIR being below 40%, may also provide inputs to the artificial pancreas application/algorithm to adjust the patient's basal rates/bolusing of drugs in order to achieve the patient's target blood glucose levels and increase the patient's time in range. The foregoing actions are intended to facilitate a more consistent time in range for the patient, which has been indicated as a reason for reduced attrition. As a result, the processes 300 and 400 increase continued use of automatic drug delivery systems.

Figure 6:
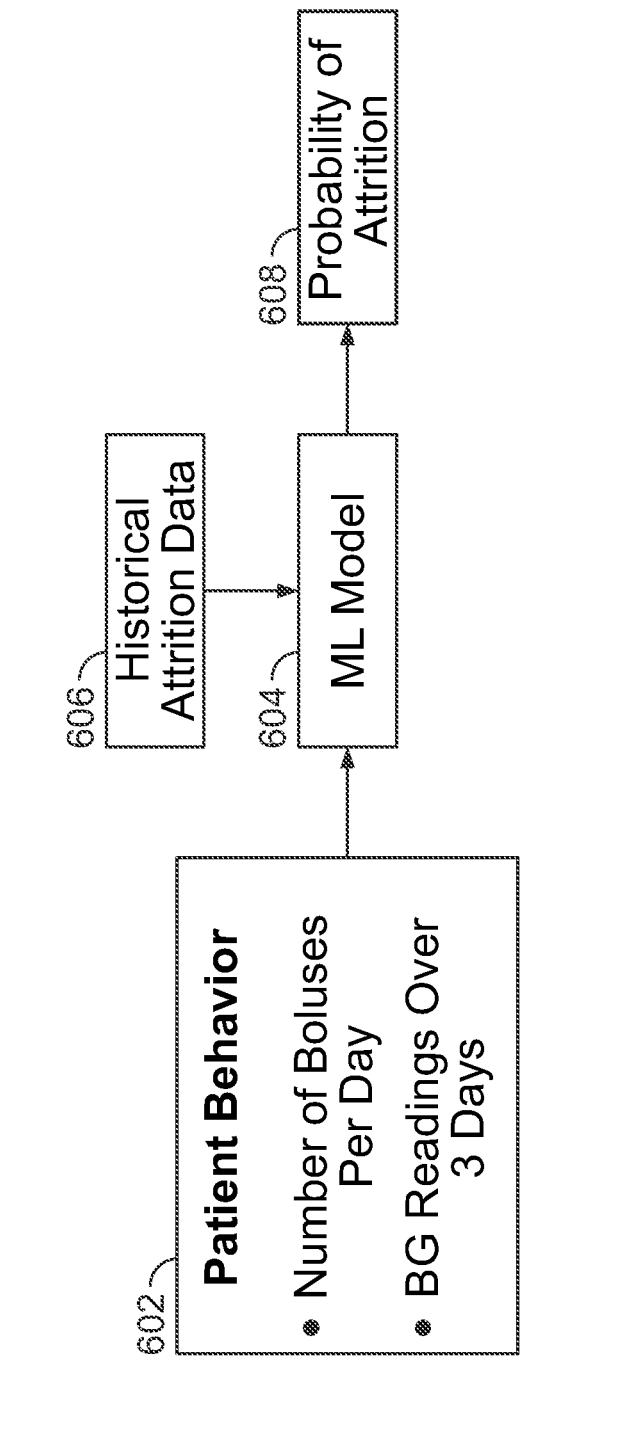
FIG. 6 illustrates an aspect of the subject matter in accordance with the disclosed embodiments.

An example of another model that may be used to process the usage-related data as well as the other data collected by the attrition prevention engine with respect to treatment and service data is a patient behavior model. FIG. 6 illustrates an example of another machine learning model usable in preventing user attrition. The premise of the patient behavior model 600 may, for example, be based on information indicating a number of bolus doses of a drug was administered per day and a number of blood glucose readings that were received by the controller.

The patient behavior model 600 evaluates the diligence shown by patients in using their drug delivery device to manage their diabetes as an important indicator of attrition. Bolusing behavior and entering blood glucose levels (via fingerstick) are two key attributes that demonstrate patient diligence. A bolus is typically taken prior to a meal. The bolus amount to be administered may depend upon the number of grams of carbohydrate in the meal, a current blood glucose value, an insulin-to-carbohydrate ratio, and the correction factor. If a bolus is not taken prior to a meal, there is an increased possibility of hyperglycemia. Further, if a blood glucose reading is not entered, the correction dose of insulin (to counteract the effects of the consumed carbohydrates) may be in error, which can again cause hyperglycemia or hypoglycemia. Historical attrition data can be used to model patient behavior with attrition probability.

The process implemented by the attrition prevention engine, when utilizing the patient behavior model 600, may evaluate the usage data provided by the controller to extract the data of interest to the patient behavior model 600. The primary data of interest is the data related to a patient maintaining their blood glucose within range, such as a number of boluses per day and the number of blood glucose readings over a period of time, such as 3 days, 36 hours, or the like. In an example, the data related to patient behavior may be extracted from the usage data 112 by an attrition prevention application executing on a controller before transmitting the usage data to the attrition prevention engine 106 in the cloud-based services 102.

The patient behavior data 602 may be evaluated by either the attrition prevention application or attrition prevention engine regarding the number of boluses per day and the number of blood glucose readings over the time period (which in this example is 3 days). The patient behavior model 600 may determine whether a continuous glucose monitor is providing the number of blood glucose readings. In some examples, the patient may not be using a CGM and the number of blood glucose readings are not being provided by the CGM.

The results of the evaluation may be input into the machine learning (ML) model 604 that has been trained using historical attrition data 606. The historical attrition data 606 may include usage-related data including use data, treatment data and service data. Respective weightings may be applied to the data based on the respective model being used in the evaluation of the data. In the example of FIG. 6, the patient behavior model 600 is being applied. When utilizing the ML model, different variables may have different weights following training of the ML model (as described above), and variables that prove more reliable or significant may be assigned larger (normalized) weights than other, less relevant variables. Results from the training of the ML model may provide a better indication (e.g., feature importance) of the class of information variables that may typically be more significant than another before results from model training are available. In a specific example of an implementation of the patient behavior model 600, the number of blood glucose readings and the number of boluses per day from the patient behavior data 602 as well as the historical attrition data 606 are weighted differently (e.g., more heavily) than other data (such as time in range) that is input into the model. Of course, different variables may be weighted differently, for example, time in range may be weighted more heavily than historical attrition data or both may be weighted equality as the results of the training are known. For example, different variables may have different weights following training the ML model (see paragraph above), and variables that prove more reliable or significant may have larger (normalized) weights than other, less relevant variables. The ML model 604 may be operable to generate a probability of attrition setting 608 (also referred to as a "probability of attrition" and the terms may be used interchangeably throughout the specification).

For example, in response to a determination that the number of blood glucose readings is being provided via another input other than by the continuous glucose monitor, either the attrition prevention application or the attrition prevention application executing the ML model 604 may establish values for rules that may be used to set the probability of attrition. For example, the values of 3 days and number of bolus doses delivered (in this example, 5 and 7) may be set in the rules. The attrition prevention application or the attrition prevention application may apply the rule to set the probability of attrition setting 608, such as:

a low probability of attrition setting if a number of bolus doses delivered over 3 days is greater than 7 (i.e., IF the number of boluses over 3 days>7 THEN the probability of attrition is LOW), a medium probability of attrition setting if a number of bolus doses delivered over 3 days is less than 7 but greater than 5 (i.e., IF 5<number of boluses over 3 days<7 THEN the probability of attrition is MEDIUM), or a high probability of attrition setting if the number of bolus doses delivered over 3 days is less than 5 (i.e., IF the number of boluses over 3 days<5 THEN the probability of attrition is HIGH).

In an example of a recommendation that results from high probability of attrition setting based on a determination of few or no bolus deliveries may be an indication of abandonment of the drug delivery device, the attrition prevention engine (APE) may notify a customer care team to reach out to follow up with the patient. In addition, the patient's healthcare provider may be alerted via email and provided with information related to the patient's low use of the drug delivery device. Reminders may be sent to the controller and other devices (e.g., laptop, a guardian's smartphone or the like) associated with the patient as an in-app (i.e., message within the attrition prevention application)/email/SMS/MMS/RCS messages to remind the patient that bolusing is important to their health management plan (which may address a user's or patient's diabetes). In addition, the in-app message and email or SMS/MMS/RCS messages may provide resources to training on how to best use the drug delivery device and contact information for a customer care team and the patient's healthcare provider. The APE in cooperation with an artificial pancreas application may implement changes to the patient's diabetes management plan, such as increasing pump usage or finding other more effective treatments in an attempt to improve the patient's time in range (TIR) and ensure the patient's overall experience with the drug delivery device is better to make attrition less likely.

Alternatively, the ML model 604 may make another determination when an input indicates the number of blood glucose readings is not being provided by the continuous glucose monitor. For example, the ML model 604 may be operable with weightings and values for a different rule that may be used to set the probability of attrition. The attrition prevention application or the attrition prevention application may apply the different rule to set the probability of attrition setting 608, such as:

a low probability of attrition setting if a number of blood glucose readings over 3 days is greater than 7 (i.e., IF the number of blood glucose readings over 3 days>7 THEN the probability of attrition is LOW), a medium probability of attrition setting if a number of blood glucose readings over 3 days is less than 7 but greater than 4 (i.e., IF 4<the number of blood glucose readings over 3 days<7 THEN the probability of attrition is MEDIUM), or a high probability of attrition setting if the number of blood glucose readings over 3 days is less than 4 (i.e., IF the number of blood glucose readings over 3 days<4 THEN the probability of attrition is HIGH).

In the example of when a patient is not using a continuous glucose monitor (CGM) and is entering blood glucose levels less than four times over any three-day period or none in any one day or, when provided with a CGM and the APE may be operable to make another determination of a high probability of attrition 608 due to blood glucose levels being entered less than once per week. The APE in response to the high probability of attrition setting may notify a customer care team to reach out to follow up with the patient. Likewise, the patient may be alerted and be provided with training materials related to open loop operation of the drug delivery device and the use of the CGM in open-loop or closed-loop operation.

The APE may also cause the delivery of in-app (i.e., attrition prevention application messages) and email or SMS/MMS/RCS messages reminding the patient that checking their blood glucose level is important to their health and diabetes management plan. The APE may follow up the in-app and email or SMS/MMS/RCS messages with additional messages that provide resources for training, and contact information for customer care and their healthcare provider. The APE may cause the generation of additional reminders or prompts for the patient to more closely follow their diabetes management plan, and reminding the patient that improved TIR results in better well-being and overall health, which results in less attrition because the patient has improved TIR.

In yet another alternative, when a patient is using a CGM and in response to the determination by either the attrition prevention engine or attrition prevention application that the number of blood glucose readings is being provided by the CGM, this information may be input into the ML model 604 with the inputs from patient behavior data 602 and historical attrition data 606. As a result, the ML model 604 may generate different values for use in the rules to set the probability of attrition. The rules applied by either the attrition prevention engine or attrition prevention application may be modified to set the probability of attrition setting 608 as follows:

a low probability of attrition setting if a number of bolus doses delivered over 3 days is greater than 7 (i.e., IF the number of boluses over 3 days>7 THEN the probability of attrition is LOW), a medium probability if a number of bolus doses delivered over 3 days is less than 7 but greater than 5 (i.e., IF 5<number of boluses over 3 days<7 THEN probability of attrition is MEDIUM), a high probability of attrition setting if the number of bolus doses delivered over 3 days is less than 4 (i.e., IF the number of boluses over 3 days<5 THEN the probability of attrition is HIGH).

Alternatively, when the attrition prevention engine or the attrition prevention application determines the number of blood glucose readings is being provided by the continuous glucose monitor, and the ML model 604 is provided with this information and the patient behavior data 602 and historical attrition data 606, the ML model 604 may provide different settings for the rules to set the probability of attrition. The different rules applied by either the attrition prevention engine or attrition prevention application may be modified to set the probability of attrition setting 608 as follows:

a low probability of attrition setting if a number of blood glucose readings over 1 week is greater than 2 (e.g., IF the number of blood glucose readings over 1 week>2 THEN the probability of attrition is LOW), a medium probability of attrition setting if a number of blood glucose readings over 1 week is less than 2 (e.g., IF the number of blood glucose readings over 1 week<2 THEN the probability of attrition is MEDIUM), or a high probability of attrition setting if the number of blood glucose readings 1 week is less than 1 (e.g., IF the number of blood glucose readings over 1 week<1 THEN the probability of attrition is HIGH).

The patient behavior model 600 utilizes data based on actions of the patient and the extent of the engagement of the patient in the determination of the probability of attrition setting 608. Other models may use data related to the product (i.e., the drug delivery device), such as amount of drug delivered, number of hours the product has been in use, or the like.

Figure 7:
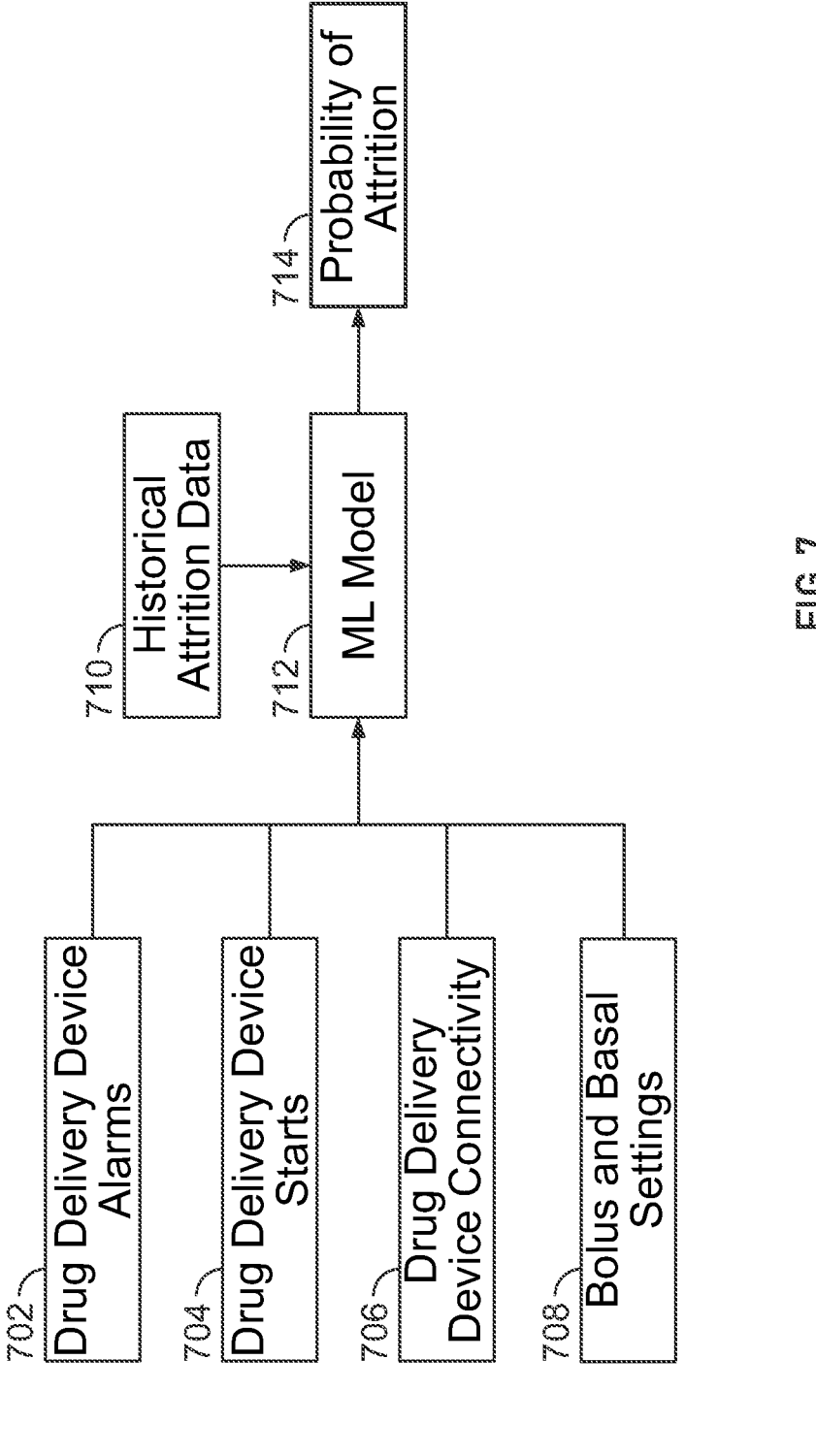
FIG. 7 illustrates an aspect of the subject matter in accordance with the disclosed embodiments.

FIG. 7 illustrates a model related to a product behavior and settings that may be implemented according to an embodiment. The product behavior and settings model may account for problems the patient may be experiencing with the drug delivery device. For example, if the drug delivery device (i.e., the product) is not behaving as expected for the patient, the patient may become disillusioned with the drug delivery device and the probability of attrition increases.

Product behavior features may include an excessive number of drug delivery device alarms 702 (such as drug delivery device failure, adhesion, occlusion, or the like), a number of drug delivery device starts in a day 704, a number of instances of poor drug delivery device connectivity 706, and poorly set bolus and basal settings 708 commonly results in higher attrition probability levels.

These different features 702, 704, 706 and 708 may be input into a ML model 712 with historical attrition data 710. The historical attrition data 710 may be used to stratify the probability of attrition based on these different features. The ML model 712 after have weightings assigned for each of respective features 702, 704, 706 and 708. For example, historical data comprising drug delivery device alarms 701, drug delivery device starts 704, poor drug delivery device connectivity 706, and poorly set bolus and basal settings 708 may be collated to yield total numbers per patient per day (daily nuisance counts). Historical usage, ordering, complaint, and other data may also be collected, yielding an estimated attrition date for patients who have stopped using the product (have attritted). Daily nuisance counts for a period preceding attrition (such as a month) may form a template for patients at risk of attrition. Daily nuisance counts for patients who are not near attrition (such as six months before attrition, or six months before the present time with no attrition in the meantime) may be used to form a template for patients not at risk of attrition. These two templates may serve as training data for a ML model that may then be used to predict attrition based on nuisance activity. The trained ML model may have weights for the respective features, and features that are more relevant may likely have larger (normalized) weights.

The process 400 may also include as part of processing the data in block 404 steps that include applying a product behavior and settings model 700 to the usage-related data. When the product behavior and settings model 700 is applied the usage-related data may include information related to product behavior features that may include an amount of time the drug delivery device maintains connectivity with the controller during a day, a number of alarms generated by the drug delivery device daily, a number of drug delivery device starts in a day, and the like.

Like the other models, the application of the product behavior and settings model includes the generation of three probability of attrition settings based on the product behavior features, the ML model 712 upon evaluating the respective inputs 702, 704, 706, 708 and 710 may output a probability of attrition setting 714.

The probability of attrition setting 714 may be set as:

a low probability of attrition setting when the amount of time the drug delivery device maintains connectivity with the controller is greater than 95 percent, the number of alarms generated by the drug delivery device daily is less than 3, and the number of delivery device starts in a day is less than 1, a medium probability of attrition setting when the amount of time the drug delivery device maintains connectivity with the controller is greater than 85 percent, the number of alarms generated by the drug delivery device daily is less than 5, and the number of delivery device starts in a day is less than 2, or a high probability of attrition setting when the amount of time the drug delivery device maintains connectivity with the controller is greater than 75 percent, the number of alarms generated by the drug delivery device daily is less than 8, and the number of delivery device starts in a day is less than 4. The controller may obtain the probability of attrition setting 714 and output the set probability of attrition setting 714 for delivery to the controller.

Figure 8A:
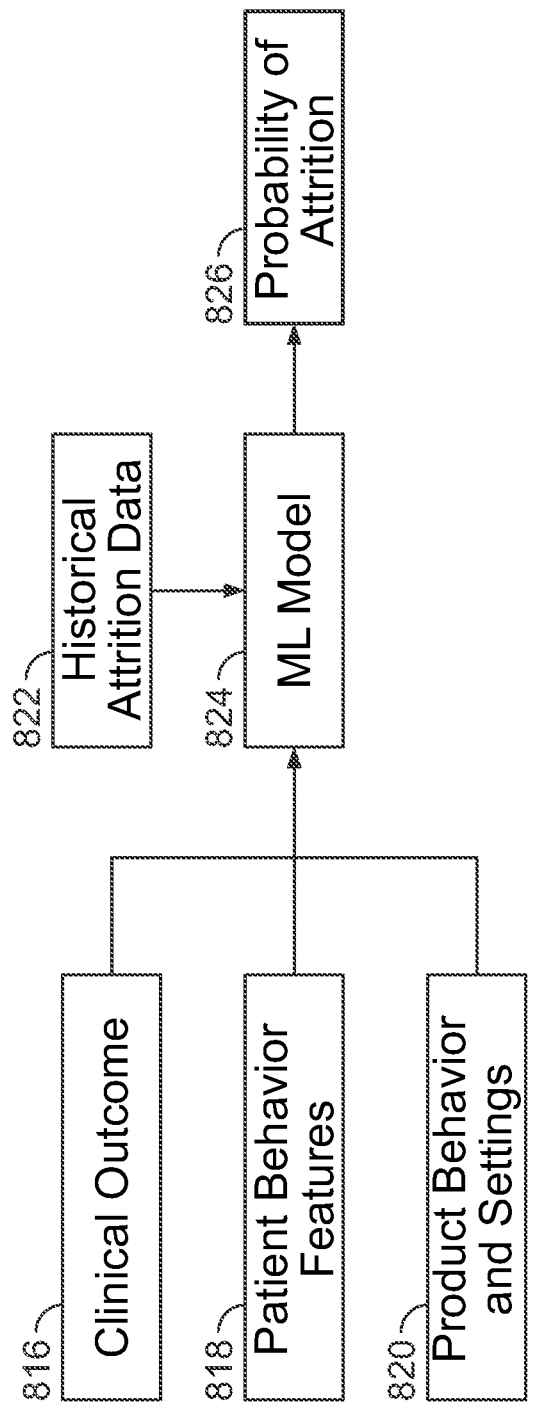
FIG. 8A illustrates an aspect of the subject matter in accordance with the disclosed embodiments.

FIG. 8A illustrates an aspect of the subject matter in accordance with the disclosed embodiments. In another alternative, elements of different models may be aggregated to form a combined attrition model that includes features from the different models discussed with reference to FIGS. 5-7. In the combined attrition model 800a, some or all the above clinical outcome features 816 of the clinical outcome model, the patient behavior features 818 of the patent behavior model and the product behavior and settings features 820 of the product behavior and settings model may be used in the determination the probability of attrition 826.

The ML model 824 may be operable to evaluate each of the different features provided by the respective models 816, 818 and 820 of the respective models. For example, the historical attrition data 822 may include historical data pertaining to each of the respective models described above with respect to FIGS. 5-7. The ML model 824 may be trained using the historical attrition data 822 to provide the correct weightings and biases on the respective inputs from the respective models 816, 818 and 820.

In an example, the attrition prevention application executing on the controller may obtain the different data related to the features 816, 818, and 820 of the respective models. The controller may provide the data related to the features 816, 818 and 820 to the attrition prevention engine. The attrition prevention engine using the ML model 824 may generate a probability of attrition setting 826. In an example, the outputs of models 816, 818 and 820 may serve as training data to model 824, which may be considered an ensemble model. Model 824 may be used as an attempt to match the attrition data. The weights of the data may depend on the relative accuracies of the three input models (816, 818 and 820) in predicting attrition, and the weightings are likely to be different across the models. For example, if the output of the clinical model 816 is more relevant in predicting attrition than that of the other models 818 and 820, then clinical model 816 would be more heavily weighted than the other models 818 and 820 in general. Similar action would happen if patient behavior model 818 (or product behavior and settings 820) was determined to be more relevant than models 816 and 820 (or 816 and 818). It is likely that the relative accuracies of the models may differ depending on the values that they respectively predict. In this case, the weighting would depend on the outputs of models 816, 818 and 820 rather than being a fixed value. For example, if the clinical model 816 is accurate when predicting a high value of attrition but not when predicting low or medium value of attrition, then it would be weighted more heavily when it predicts high values of attrition rather than other values of attrition. Similar, biasing of weightings would apply to the outputs of the models 818 and 820 depending upon the prediction accuracy of the respective models. The process may be similar to those described with reference to FIGS. 3 and 4.

Figure 8B:
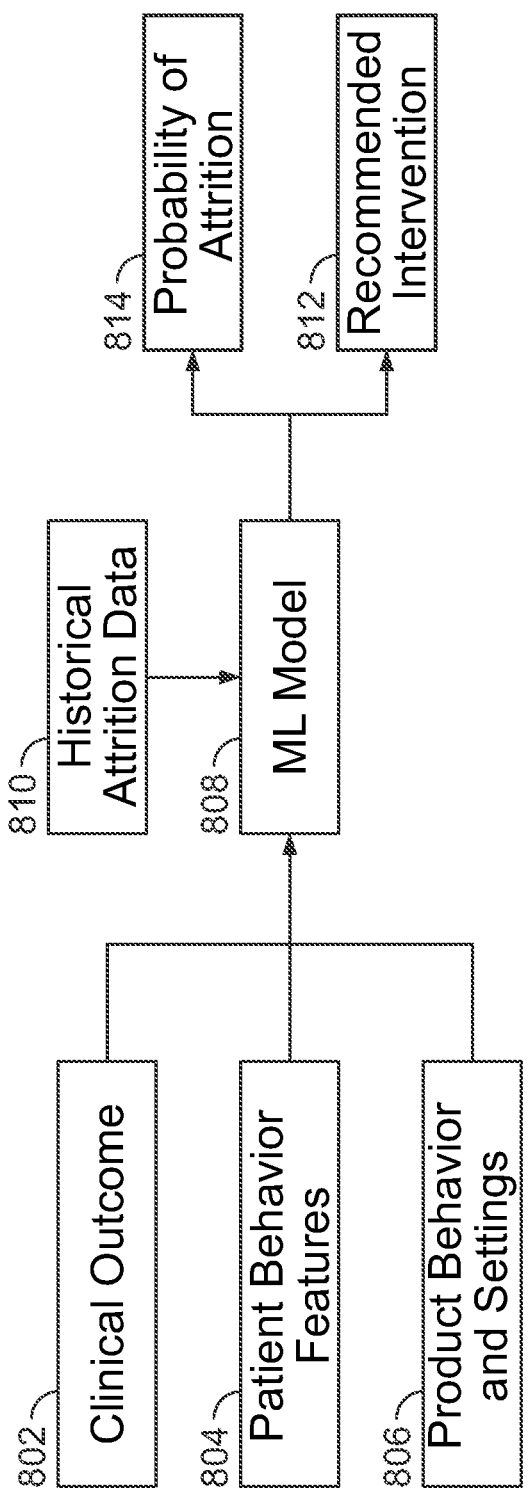
FIG. 8B illustrates an aspect of the subject matter in accordance with the disclosed embodiments.

FIG. 8B illustrates an aspect of the subject matter in accordance with the disclosed embodiments. In another alternative, elements of different models may be aggregated to form a combined attrition model that includes features from the different models discussed with reference to FIGS. 5-7. In the combined attrition model 800b, some or all of the above clinical outcome features 802 of the clinical outcome model, the patient behavior features 804 of the patent behavior model and the product behavior and settings features 806 of the product behavior and settings model may be used in the determination the probability of attrition 814 as well as a recommended intervention 812.

In the combined attrition model 800b, some or all the above clinical outcome features 802 of the clinical outcome model, the patient behavior features 804 of the patent behavior model and the product behavior and settings features 806 of the product behavior and settings model may be used in the determination the probability of attrition 814 and the recommended intervention 812.

The ML model 808 may be operable to evaluate each of the different features provided by the respective models 802, 804 and 806. For example, the historical attrition data 810 may include historical data pertaining to each of the respective models described above with respect to FIGS. 5-7. The ML model 808 may be trained using the historical attrition data 810 to provide the correct weightings and biases on the respective inputs from the respective models 802, 804 and 806.

In an example, the attrition prevention application executing on the controller may obtain the different data related to the features of the respective models 802, 804 and 806. The controller may provide the data related to the models 802, 804 and 806 to the attrition prevention engine. The attrition prevention engine using the ML model 808 may generate a probability of attrition setting 814. The outcome 814 may be identical to the outcome 826, and the above description applies. The ML model 808 thus incorporates the ML model 824 as part of its functionality, namely the part that generates 826. Models 506, 604, and 712 as described above may each be augmented to predict the recommended intervention as well as the probability of attrition. These models may be trained on the inputs already shown in their respective figures, including historical attrition data, but also the history of interventions attempted. These augmented data sets serve as training data, yielding an ML model able to predict the best intervention. The predicted best interventions, and the predicted probability of attrition, may serve as training data to the ML model 808. In this example, ML model 808 may combine its assorted inputs as delineated above to yield a best overall recommended intervention. In addition, the combined ML model 808 may select a potential attrition reason and intervention modality as described below. The process may be similar to those described with reference to FIGS. 3 and 4. The notification with recommendation discussed with reference to the processes 300 and 400 of FIGS. 3 and 4, are described below with reference to the recommended intervention 812.

In some examples as part of recommended intervention 812, the notification and recommendation may include instructions for actions to be taken by the attrition prevention application. The content of the instructions may be based on a potential attrition reason indicated by the probability of attrition setting (regardless of the model used). The probability of attrition setting, and intervention modality may be provided by the attrition prevention engine and/or the attrition prevention application. The intervention modality may be different actions taken by the controller in response to commands from the attrition prevention application. The intervention modality if followed by the patient is intended to not only reduce attrition of the patient from using the drug delivery device, but also help the patient maintain within the settings of their health management plan, for example, by increasing their time in range of their blood glucose settings. For example, the attrition prevention engine and/or the attrition prevention application may generate the instructions related to the intervention in response to the recommended intervention 812 and probability of attrition 814. The instructions when received at the controller may cause the attrition prevention application executed by the controller to monitor the basal rates and bolus amounts set by an artificial pancreas application and suggest modifications thereto. The suggested modifications may be to the actual basal rates or bolus amounts or may be modifications to parameters used to calculate the basal rates and bolus amounts. For example, if the patient behavior model causes the generation of the instructions the instructions may prompt the patient to deliver more bolus dosages.

The probability of attrition setting and the underlying reasons for attrition that contribute to the probability of attrition setting produced by any of the models described with reference to FIGS. 5-8B may be used to direct interventions for the patient from the customer care system 118, which may include input from a clinical team (e.g., an information provider that assists with the health related aspects of living with diabetes), a product support team (e.g., an information provider that assists with utilizing the drug delivery device to its full potential for the patient's needs), and a marketing team (e.g., an information provider that assists the patient with obtaining the most value from the use of the drug delivery device). For example, the interventions may be sent to the controller using in-app (i.e., within the attrition prevention application) messages, phone calls (over a cellular network), user alerts via messaging protocols such as SMS/MMS/RCS, or the like. The direct interventions may be tips or suggestions on using the drug delivery device more efficiently with regard to the clinical, product support and marketing aspects for a given patient. The specific direct intervention may include communications from one or more of the clinical team, the product support team and the marketing team.

Each of the processes 300 and 400 refer to generating a notification or a recommendation with transmitting instructions. As mentioned above with respect to process 300, the response indicated in the notification may include instructions for the attrition prevention application to execute, while the generated recommendation in process 400 may include instructions that are implemented by the attrition prevention application. In an example using the model of FIG. 8B, the instructions may cause the attrition prevention application executing on the controller to generate a prompt for presentation on a touchscreen display with preset text informing the patient of actions the patient may take to optimize the use of their drug delivery device. The same instructions may cause the attrition prevention application to cause an artificial pancreas application to make modifications to drug delivery dosages and times that are controlled by the artificial pancreas application, and the like.

As described with reference to the respective examples of FIG. 5-8B, different scenarios may occur that cause or have reasons given for a user to no longer use a drug delivery device. The notifications may include a probability of attrition setting that corresponds to the different scenarios. Based on the recommended intervention may be classified as determining a probability of attrition setting based on inputs from the user (e.g., skipping a bolus, taking actions following advice about a bolus dosage or the like), actions taken by the user (e.g., contacting customer with a question, turning off the attrition prevention application, engaging the attrition prevention application to discover features of the drug delivery device or the like), receiving data from the drug delivery device and an analyte sensor, such as a blood glucose sensor, or a continuous glucose monitor (CGM), or the like. Based on the determined attrition setting, the attrition prevention engine may determine a response. The response may include generating different alerts to deliver to an enterprise, a user or a health care professional. Based on the response, modifications to a treatment program for the specific user may be determined and implemented in an attempt to achieve a target blood glucose level as well as improving the patient's time in range with respect to the target blood glucose level. For example, a more consistent time in range has been indicated as a reason for reduced attrition.

In an example related to the use of the combined attrition model 800*b* in FIG. 8B, a probability of attrition setting may be set to high in response to a determination that the basal settings and/or bolus amounts of the artificial pancreas application are within 5% of maximum drug delivery device limits. The APE may notify a customer care team to reach out to follow up with the patient. The patient's healthcare provider may be alerted, for example, via email and provided with a view of the patient's insulin usage, the patient's blood glucose value history, and other relevant data (e.g., time in range, average blood glucose value or the like). In addition, the patient may be provided with in-application (i.e., attrition prevention application) messages and/or an email or an SMS/MMS messages requesting verification of the extreme insulin use. Further, the messages or email or SMS/MMS message may provide resource information including customer care and healthcare provider contact information, and links to websites and videos indicating the potential risks of extreme insulin delivery. The APE as part of the artificial pancreas application or algorithm may request adjustment of basal rates/bolusing to achieve target blood glucose levels and increase the patient's time in range. The extreme delivery of insulin may be due to a patient's lack of understanding of the operation of the drug delivery device and effects of too much insulin on the body. A better understanding of how to use the drug delivery device has been shown in reduce attrition.

An example of the patient behavior features 804 may be another of times a patent uploads treatment-related information. In an example, another medium or high probability of attrition setting determination may result in generation of a recommended intervention in response to a determination the patient has not made any uploads of treatment-related information in the last three weeks. In response to a determination by the APE of a high probability of attrition setting, the APE may notify a customer care team to reach out to follow up with the patient to explain the benefits of data upload to personalized treatment. The APE may also be alerted to the loss of opportunity to fine-tune treatment. The APE may cause the generation and delivery of in-app and email or SMS/MMS messages intended to motivate the patient to increase the frequency of their data uploads. The APE may also generate and cause delivery of a troubleshooting guide and other resources, such as contact information for a customer care team. The APE response is intended to provide increased adherence to the patient's diabetes management plan and increased/improved usage of the drug delivery device which likely leads to better insulin and diabetes management as well as less attrition.

A further example of a probability of attrition setting determination made using the combined attrition model 800*b* may be when a patient uploads data showing more than one day between an end of using one drug delivery device and the beginning of using a next drug delivery device. In response to such a determination resulting in a probability of attrition setting being medium or high, the APE may notify a customer care team to reach out to follow up with the patient to explain the benefits of data upload to personalized treatment. The APE may also generate and cause delivery of alerts via in-app/email/SMS/MMS messages that may point to application videos that explain the detrimental effects of low adherence to the use of a drug delivery device. The in-app/email/SMS/MMS messages may inquire of the patient whether they have used their drug delivery device recently and may also provide resources (e.g., contact information or links to websites or the like) to training, customer care, and their healthcare provider on how to use the drug delivery device. For example, the provided resources may explain the benefits of increased pump usage or enable the patient to find other treatments that for the patient may be more effective at improving TIR. The APE in response to such a determination of this attrition setting may be operable to initiate changes to the patient's diabetes management plan. This attrition setting causes a response that is a targeted intervention that may potentially prevent attrition of the patient.

Yet another probability of attrition setting determination made using the combined attrition model 800*b* may be that the patient has attempted more than three drug delivery device starts in one day. In response to this probability of attrition setting being medium or high, the APE may notify a customer care team to reach out to a follow up with the patient. The APE may generate and cause delivery of in-app (i.e., attrition prevention application)/email/SMS/MMS messages asking if the patient is having drug delivery device issues and provide resources to training and customer care. The APE may also be operable to initiate changes to a patient's diabetes management plan that optimize usage of a drug delivery device. In response to the optimized usage, the patient may increase pump usage which since it has been optimized has improved the patient's TIR. Hence, attrition is less likely due to better TIR, reduced frustration on the patient's part, and better understanding by the patient of how to use the drug delivery device.

There may be different types of failures of the drug delivery device, such as general failure, adhesion failure, or occlusion failure. An attrition setting may be a general failure alert. In the case of the general failure, an alert may be generated notifying a customer care team to reach out as a follow up with the patient. The notification may also indicate to a user that a replacement drug delivery device is available. A healthcare provider may or may not be notified. In addition, in-app/email/SMS/MMS messages may be delivered that provide a troubleshooting guide as well as resources to reach out to the customer care team. The notification may remind the patient that increased time using the drug delivery device typically leads to better diabetes management. The results of the general failure notification may be that attrition is less likely due to better TIR and reduced frustration with the drug delivery device.

The other example of a drug delivery device failure is a failure of adhesion. An alert notifying the patient of the adhesion failure may provide information about skin preparation before applying drug delivery device or an offer of contacting other users of a drug delivery device who may offer support (e.g., such as a mentor or tutor) for using the drug delivery device. The healthcare provider may or may not be contacted. The notification provided to the patient may include information about general drug delivery device failures related to adhesion. The intention of the notification is to increase the amount of time a patient is using the drug delivery device, which leads to better diabetes management. As a result, attrition is hopefully less likely due to better TIR and reduced frustration with the product.

Another example of a drug delivery device failure is a failure due to occlusion. An occlusion failure may result from various reasons related to the manufacture of the drug delivery device or of a site where the drug delivery device is adhered to the user. An example of a manufacturing error related to the drug delivery device may be a problem with a needle/cannula, a drug pathway between a drug reservoir and the needle/cannula, or the like. A site location problem may be the presence of too much scar tissue at the site location which slows or prevents delivery of the drug, or other problems that do not permit the drug to be effectively delivered. In response to such an alert, the APE may generate a notification of a general drug delivery device failure. The APE may also inquire with an enterprise system server related to drug delivery device recalls or noted manufacturing issues with a version or manufacturing lot of drug delivery devices. If there is a recall or other issue flagged in response to the inquiry to the enterprise system server, the APE will notify the patient. For example, an issue such as a cross drilling failure may result in replacement of remaining drug delivery devices. The healthcare provider may or may not be notified of a drug delivery failure. An occlusion drug delivery device failure notification to a patient may include links to information about different techniques, such "pinching up," to use before applying the drug delivery device to an adhesion site. This type of notification is intended to increase time using the drug delivery device, which leads to better diabetes management and less attrition due to better TIR and reduced frustration with the drug delivery device.

Another example of a probability of attrition setting being medium or high may occur in the combined attrition model 800b when an enterprise system determines a patient has made more than two calls to customer care in one week. As a result, the APE may monitor engagements with the Customer care system 118 to ensure proper follow-up has occurred from previous calls. For example, the APE may generate an inquiry to the controller to determine if messages have been received from the customer care team regarding the patient's calls. For example, the messages may be responses addressing the patient's reasons for calling and may be inquiries as to whether the patient's concerns have been properly addressed. The APE may also provide the customer care team with information related to the patients concerns that prompted the two calls to customer care. The APE may also cause the delivery of in-app/email/SMS/ MMS messages that provide providing a troubleshooting guide directed to the patient's concerns expressed in the two calls. The intention is to retain the patient as a user of the drug delivery device since it has been shown continued use leads to continued improvement of the patient's diabetes management and prevention of worse outcomes due to attrition. In addition, a patient is likely to have a better customer care experience and have reduced frustration with the drug delivery device.

Figure 9:
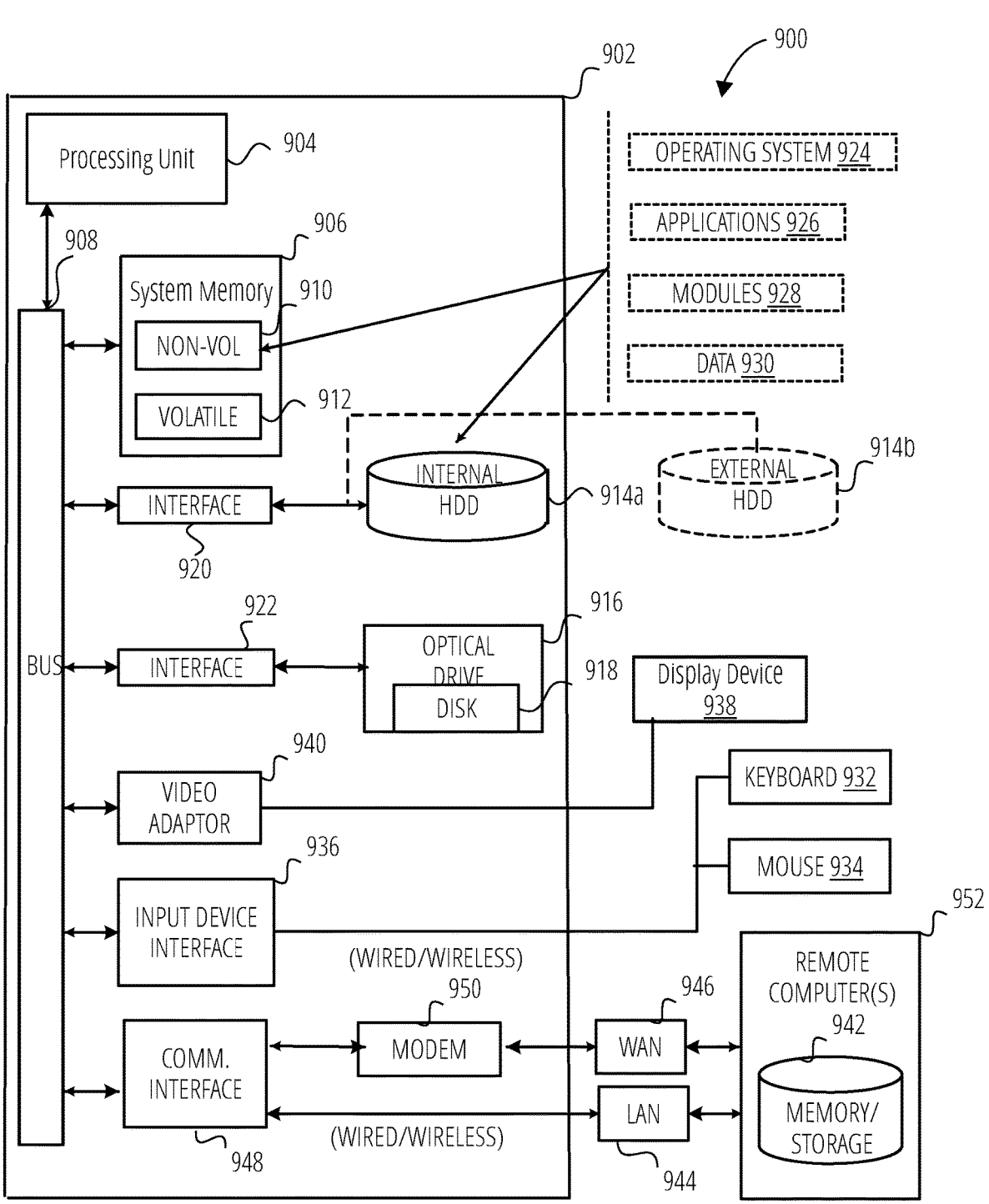
FIG. 9 illustrates an aspect of the subject matter in accordance with the disclosed embodiments.

FIG. 9 illustrates an embodiment of an exemplary computing architecture 900 suitable for implementing various embodiments as previously described. In one example, the computing architecture 900 may include or be implemented as part of system 100. In another example, the computer architecture 900 includes components of cloud-based services, stakeholder systems, a controller and the like.

The computing architecture 900 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 900.

As shown in FIG. 9, the computing architecture 900 includes a processing unit 904, a system memory 906 and a system bus 908. The processing unit 904 can be any of various commercially available processors. The one or more of the components of the computer architecture 900 may be incorporated in the controller 134, cloud-based services 102 and Stakeholder system 104 of FIG. 1A.

The system bus 908 provides an interface for system components including, but not limited to, the system memory 906 to the Processing unit 904. The system bus 908 can be any of several types of bus structure that may further interconnect to a memory bus (with or without a memory controller), a peripheral bus, and a local bus using any of a variety of commercially available bus architectures. Interface adapters may connect to the system bus 908 via slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The computing architecture 900 may include or implement various articles of manufacture. An article of manufacture may include a non-transient computer-readable storage medium to store logic. Examples of a computer-readable storage medium may include any tangible media capable of storing electronic data, including volatile memory or nonvolatile memory, removable or non-removable memory, erasable or non-erasable memory, writeable or re-writeable memory, and so forth. Examples of logic may include executable computer program instructions implemented using any suitable type of code, such as source code, compiled code, interpreted code, executable code, static code, dynamic code, object-oriented code, visual code, and the like. Embodiments may also be at least partly implemented as instructions contained in or on a non-transitory computer-readable medium, which may be read and executed by one or more processors to enable performance of the operations described herein.

The system memory 906 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. The system memory 906 can include non-volatile memory 910 and/or volatile memory 912. A basic input/output system (BIOS) can be stored in the non-volatile memory 910.

The computer 902 may include various types of computer-readable storage media in the form of one or more lower speed memory units, including an internal hard disk drive (HDD) 914a or external HDD 914b, and an optical disk drive 916 to read from or write to a removable optical disk 918 (e.g., a CD-ROM or DVD). The internal HDD 914a and optical disk drive 916 can be connected to the system bus 908 by an HDD interface 920 and an optical drive interface 922, respectively. The HDD interface 920 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, several program modules can be stored in the drives and memories 910, 912, including an operating system 924, one or more application programs 926, other program modules 928, and program data 930. In one embodiment, the one or more application programs 926, other program modules 928, and program data 930 can include, for example, the various applications and/or components of the system 100 of FIG. 1A.

A user can enter commands and information into the computer 902 through one or more wired/wireless input devices, for example, a keyboard 932 and a pointing device, such as a mouse 34. Other input devices that may replace or complement keyboard 932 and/or mouse 934 may include microphones, infra-red (IR) remote controls, radio-frequency (RF) remote controls, game pads, stylus pens, card readers, dongles, fingerprint readers, gloves, graphics tablets, joysticks, keyboards, retina readers, touch screens (e.g., capacitive, resistive, etc.), trackballs, track pads, sensors, styluses, and the like. These and other input devices are often connected to the processing unit 904 through an input device interface 936 that is coupled to the system bus 908 but can be connected by other interfaces such as a parallel port, IEEE 1394 serial port, a game port, a USB port, an IR interface, and so forth.

A display device 938 or another type of display device is also connected to the system bus 908 via an interface, such as a video adapter 940. The display device 938 may be internal or external to the computer 902. In addition to display device 938, a computer typically includes other peripheral output devices, such as speakers, printers, and so forth.

The computer 902 may operate in a networked environment using logical connections via wire and/or wireless communications to one or more remote computers, such as a remote computer 952. The remote computer 952 can be a workstation, a server computer, a router, a personal computer, portable computer, microprocessor-based entertainment appliance, a peer device or other common network node, and typically includes many or all the elements described relative to the computer 902, although, for purposes of brevity, only a remote memory/storage device 942 is illustrated. The logical connections depicted include wire/wireless connectivity to a local area network (LAN) 944 and/or larger networks, for example, a wide area network (WAN) 946. Such LAN and WAN networking environments are commonplace in offices and companies and facilitate enterprise-wide computer networks, such as intranets, all of which may connect to a global communications network, for example, the Internet.

For example, identity and e-signature verification system implemented according to the example of FIG. 9 may authenticate the identity of one or more users related to transactions stored at an address in the blockchain. As explained through the description of the examples of FIGS.

1-5, the combination of using an electronic signature application provided by an enterprise and an identity and electronic signature verification system as provided by the enterprise provides a level of security and service from the enterprise that is presently unavailable. An instance of the electronic signature application may be stored in memory 906 or any one of the internal HDD 914a or external HDD 914b, usable to implement the hardware and process examples described with reference to FIGS. 1A-9 above.

When used in a LAN networking environment, the computer 902 is connected to the LAN 944 through a communication interface 948 that may be either wired and/or wireless. The communication interface 948 can facilitate wired and/or wireless communications to the LAN 944, which may also include a wireless access point disposed thereon for communicating with the wireless functionality of the communication interface 948.

When used in a WAN networking environment, the computer 902 can include a modem 950, or is connected to a communications server on the WAN 946 or has other means for establishing communications over the WAN 946, such as by way of the Internet. The modem 950, which can be internal or external and a wire and/or wireless device, connects to the system bus 908 via the input device interface 936. In a networked environment, program modules depicted relative to the computer 902, or portions thereof, can be stored in the remote memory/storage device 942. It will be appreciated that the network connections shown are exemplary and other means of establishing a communications link between the computers can be used.

The computer 902 may also be implemented in a cloud-based platform and be operable to provide the servers and other components described with reference to cloud-based services 102 of FIG. 1A.

The computer 902 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth® wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

The various elements of the devices, apparatuses or systems as previously described with reference to FIGS. 1A-9 may include various hardware elements, software elements, or a combination of both. Examples of hardware elements may include structural members, logic devices, components, processors, microprocessors, circuits, processors, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), memory units, logic gates, registers, semiconductor device, chips, microchips, chip sets, and so forth. Examples of software elements may include software components, programs, applications, computer programs, application programs, system programs, software development programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof.

As used in this application, the terms "system" and "component" are intended to refer to a computer-related entity, either hardware, a combination of hardware and software, software, or software in execution, examples of which are provided by the exemplary computing architecture 900. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data transactions. Such data transactions may be sent across various connections. Exemplary connections include parallel interfaces, serial interfaces, and bus interfaces.

While the foregoing aspects of the disclosed subject matter are described with reference to a drug delivery device that is a wearable drug delivery device, the described processes and techniques are also relevant to tube systems as well. Other technical features may be readily apparent to one skilled in the art from the following figures, descriptions, and claims.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

What is claimed is:

1. A treatment plan management system, comprising:
   a drug delivery device operable to expel a drug according to a programmed drug treatment plan;
   an analyte sensor operable to measure analytes in blood of a patient and output signals related to analyte measurement values of the measured analytes;
   a controller operable to provide control commands to the drug delivery device, receive inputs from the drug delivery device and the analyte sensor, and execute an attrition prevention application; and
   a server communicatively coupled with the controller and a data storage and operable to execute an attrition prevention engine, wherein the server executing the attrition prevention engine is operable to:
      receive status signals from the controller;
      compare the received status signals to status signals stored in the data storage;
      based on a result of the comparing, generate a notification indicating a response to be generated by the attrition prevention engine; and
      forward the notification to the attrition prevention application for implementation of the response.

2. The system of claim 1, wherein the received status signals include usage information related to analyte measurement values, information related to delivery of the drug to the patient, and information related to patient interactions with the programmed drug treatment plan.

3. The system of claim 1, wherein the analyte sensor further comprises:
   a blood glucose detector, wherein an analyte measurement value is a blood glucose measurement value.

4. The system of claim 1, wherein the drug delivery device includes:
   a processor,
   a memory storing programming code executable by the processor,
   a drug container configured to contain a liquid drug,
   a pump drive mechanism operable to expel the liquid drug from the drug container, and
   a communication device coupled to the processor and operable to wirelessly communicate with one or more devices.

5. The system of claim 4, wherein
   the processor is operable when executing the programming code to:
      establish a wireless communication link via the communication device with the controller; and
      output measurement values obtained by the analyte sensor via the communication device for delivery to the controller via the wireless communication link.

6. The system of claim 1, wherein the analyte sensor includes:
   a transceiver operable to wirelessly communicate with the drug delivery device and other devices;
   one or more detectors respectively operable to measure parameters related to one or more analyte of the patient; and
   logic circuitry coupled to the transceiver and the one or more detectors, the logic circuitry operable to control the analyte sensor and the transceiver.

7. The system of claim 1, wherein the server is operable when comparing the received status signals to previously-received status signals stored in the data storage to:
   identify a match between the received signals and a set of signals in the previously-received status signals;
   locate instructions in the data storage that correspond to the set of previously-received status signals identified as matching the received signals; and
   use the instructions in the generation of the notification and the indicated response.

8. The system of claim 7, wherein the server is further operable when executing the programming code to:
   receive a request for details of the indicated response from the controller; and provide the details of the indicated response to the controller.

9. The system of claim 1, wherein the controller further comprises:

a controller processor, a memory, a communication device and a user interface, wherein the user interface is operable to present information and receive the inputs to the controller and the controller processor is operable to:

output to the user interface a user notification with resource information;

receive via the user interface a selection of a contact within the resource information;

in response to the selection, implement a communication session via the communication device; and based on a result of the communication session, modify drug delivery settings of the drug delivery device, wherein the modified drug delivery settings are selected based on a likelihood of achieving a patient's target blood glucose levels and improving a time in range of a blood glucose target of the patient.

10. The system of claim 9, wherein the controller processor is further operable, when modifying the drug delivery settings of the drug delivery device, to:

adjust basal rate doses or bolus doses of the liquid drug.

11. The system of claim 9, wherein the controller processor is further operable to:

determine a basal rate dose that given information obtained from the received status signals is intended to achieve a target blood glucose level for the patient and increase an amount of time in range of the target blood glucose level; and cause delivery of the determined basal rate dose when controlling the drug delivery device according to the modified drug delivery settings.

12. The system of claim 9, wherein the controller processor is further operable to:

determine a bolus dose that given information obtained from the received status signals is intended to achieve a target blood glucose level for the patient and increase an amount of time in range of the target blood glucose level; and cause delivery of the determined bolus dose when controlling the drug delivery device according to the modified drug delivery settings.

13. The system of claim 9, wherein the controller processor is further operable to:

determine both a basal rate dose and a bolus dose that given information obtained from the received status signals are intended to achieve a target blood glucose level for the patient and increase an amount of time in range of the target blood glucose level; and cause delivery of the determined basal rate dose and determined bolus dose when controlling the drug delivery device according to the modified drug delivery settings.

\* \* \* \* \*